United States Patent
Oliphant et al.

(10) Patent No.: US 10,131,947 B2
(45) Date of Patent: Nov. 20, 2018

(54) NONINVASIVE DETECTION OF FETAL ANEUPLOIDY IN EGG DONOR PREGNANCIES

(71) Applicant: Ariosa Diagnostics, Inc., San Jose, CA (US)

(72) Inventors: Arnold Oliphant, San Jose, CA (US); Eric Wang, San Jose, CA (US); Craig Struble, San Jose, CA (US)

(73) Assignee: ARIOSA DIAGNOSTICS, INC., San Jose, CA (US)

( * ) Notice: Subject to any disclaimer, the term of this patent is extended or adjusted under 35 U.S.C. 154(b) by 1089 days.

(21) Appl. No.: 13/720,273

(22) Filed: Dec. 19, 2012

(65) Prior Publication Data

US 2013/0178371 A1    Jul. 11, 2013

Related U.S. Application Data

(63) Continuation-in-part of application No. 13/338,963, filed on Dec. 28, 2011, now Pat. No. 8,700,338, which is a continuation-in-part of application No. 13/316,154, filed on Dec. 9, 2011.

(60) Provisional application No. 61/436,135, filed on Jan. 25, 2011.

(51) Int. Cl.
| | |
|---|---|
| *C12Q 1/68* | (2018.01) |
| *G06F 19/22* | (2011.01) |
| *C12Q 1/6883* | (2018.01) |
| *C12Q 1/6809* | (2018.01) |
| *G06F 19/18* | (2011.01) |

(52) U.S. Cl.
CPC ......... *C12Q 1/6883* (2013.01); *C12Q 1/6809* (2013.01); *C12Q 2600/156* (2013.01); *G06F 19/18* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,988,617 A | 1/1991 | Landegren et al. | |
| 5,143,854 A | 9/1992 | Pirrung et al. | |
| 5,242,794 A | 9/1993 | Whiteley et al. | |
| 5,270,184 A | 12/1993 | Walker et al. | |
| 5,399,491 A | 3/1995 | Kacian et al. | |
| 5,409,818 A | 4/1995 | Davey et al. | |
| 5,413,909 A | 5/1995 | Bassam et al. | |
| 5,422,252 A | 6/1995 | Walker et al. | |
| 5,437,975 A | 8/1995 | McClelland | |
| 5,494,810 A | 2/1996 | Barany et al. | |
| 5,547,839 A | 8/1996 | Dower et al. | |
| 5,554,517 A | 9/1996 | Davey et al. | |
| 5,578,832 A | 11/1996 | Trulson et al. | |
| 5,631,734 A | 5/1997 | Stern et al. | |
| 5,648,245 A | 7/1997 | Fire et al. | |
| 5,800,992 A | 9/1998 | Fodor et al. | |
| 5,808,041 A | 9/1998 | Padhye et al. | |
| 5,830,711 A | 11/1998 | Barany et al. | |
| 5,834,758 A | 11/1998 | Trulson et al. | |
| 5,856,092 A | 1/1999 | Dale et al. | |
| 5,861,245 A | 1/1999 | McClelland et al. | |
| 5,871,928 A | 2/1999 | Fodor et al. | |
| 5,874,219 A | 2/1999 | Rava et al. | |
| 5,876,924 A | 3/1999 | Zhang et al. | |
| 5,888,740 A | 3/1999 | Han | |
| 5,898,071 A | 4/1999 | Hawkins | |
| 5,902,723 A | 5/1999 | Dower et al. | |
| 5,936,324 A | 8/1999 | Montagu | |
| 5,952,170 A | 9/1999 | Stroun et al. | |
| 5,981,956 A | 11/1999 | Stern | |
| 6,025,601 A | 2/2000 | Trulson et al. | |
| 6,027,889 A | 2/2000 | Barany et al. | |
| 6,045,996 A | 4/2000 | Cronin et al. | |
| 6,054,564 A | 4/2000 | Barany et al. | |
| 6,063,603 A | 5/2000 | Davey et al. | |
| 6,090,555 A | 7/2000 | Fiekowsky et al. | |
| 6,136,229 A | 10/2000 | Cui et al. | |
| 6,141,096 A | 10/2000 | Stern et al. | |
| 6,156,504 A | 12/2000 | Gocke et al. | |
| 6,185,030 B1 | 2/2001 | Overbeck | |
| 6,201,639 B1 | 3/2001 | Overbeck | |
| 6,210,891 B1 | 4/2001 | Nyren et al. | |

(Continued)

FOREIGN PATENT DOCUMENTS

| | | |
|---|---|---|
| EP | 1-591-534 A1 | 11/2005 |
| GB | 2299166 | 9/1996 |

(Continued)

OTHER PUBLICATIONS

Mardis (Mardis, E. (2008) Annual Review of Genomics and Human Genetics, 9:387-402).*
Dhallan et al. "A non-invasive test for prenatal diagnosis based on fetal DNA present in maternal blood: a preliminary study", Lancet, 369 (9560): 474-481.*
Search Report dated Aug. 12, 2014 for PCT/US2013/75683, entire document.
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian.Translocations", Am J. Hum Genet., 50:717-24 (1992).

(Continued)

*Primary Examiner* — John S Brusca
(74) *Attorney, Agent, or Firm* — Mintz Levin Cohn Ferris Glovsky and Popeo, P.C.

(57) ABSTRACT

The present invention provides assay systems and methods for determining the percent fetal contribution of cell-free DNA in a maternal sample from a pregnant female with an egg donor pregnancy. Further provided, are assay systems and methods for determining a statistical likelihood of the presence or absence of a fetal aneuploidy in a maternal sample using a determined percent fetal cell-free DNA in the sample.

19 Claims, 5 Drawing Sheets

(56) References Cited

U.S. PATENT DOCUMENTS

| | | | |
|---|---|---|---|
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Lo |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,293,076 B2 | 10/2012 | Fan et al. |
| 8,318,430 B2 | 11/2012 | Chuu et al. |
| 8,700,338 B2 | 4/2014 | Oliphant et al. |
| 2002/0045176 A1 | 4/2002 | Lo |
| 2002/0132241 A1* | 9/2002 | Fan ............... C12Q 1/6809 |
| | | 435/6.18 |
| 2003/0003459 A1 | 1/2003 | Stahl |
| 2003/0044388 A1 | 3/2003 | Lo et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0101835 A1 | 5/2004 | Willis et al. |
| 2004/0203037 A1 | 10/2004 | Lo et al. |
| 2004/0214175 A9 | 10/2004 | McKernan et al. |
| 2005/0095618 A1 | 5/2005 | Tsuio et al. |
| 2005/0191656 A1 | 9/2005 | Drmanac et al. |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0096766 A1 | 4/2008 | Lee |
| 2008/0138809 A1 | 6/2008 | Kapur et al. |
| 2008/0206749 A1 | 8/2008 | Lo et al. |
| 2008/0243398 A1 | 10/2008 | Rabinowitz |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1* | 4/2009 | Lo .................. G06F 19/18 |
| | | 435/6.12 |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124515 A1 | 5/2011 | Silver |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0039724 A1 | 2/2012 | Rossi |
| 2012/0053062 A1 | 3/2012 | Brooks |
| 2012/0100548 A1 | 4/2012 | Rava et al. |

(56) References Cited

U.S. PATENT DOCUMENTS

| | | |
|---|---|---|
| 2012/0108460 A1 | 5/2012 | Quake et al. |
| 2012/0122701 A1 | 5/2012 | Ryan et al. |
| 2012/0165203 A1 | 6/2012 | Quake et al. |
| 2012/0184449 A1 | 6/2012 | Hixson |
| 2012/0190557 A1 | 7/2012 | Oliphant et al. |
| 2012/0191359 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0225798 A1 | 9/2012 | Cantor et al. |
| 2012/0230258 A1 | 9/2012 | Miki |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |
| 2013/0029852 A1 | 1/2013 | Rava |
| 2013/0178371 A1 | 7/2013 | Oliphant et al. |

FOREIGN PATENT DOCUMENTS

| | | |
|---|---|---|
| GB | 97044 | 3/1997 |
| WO | WO87/006270 | 10/1987 |
| WO | WO90/06995 | 6/1990 |
| WO | WO99/47964 | 9/1999 |
| WO | WO2003/038120 | 5/2003 |
| WO | WO-2005/035725 A2 | 4/2005 |
| WO | WO-2005/035725 A3 | 4/2005 |
| WO | WO2007/100243 | 9/2007 |
| WO | WO2007/126377 | 11/2007 |
| WO | WO2008/118998 | 10/2008 |
| WO | WO2009/036525 | 3/2009 |
| WO | WO2009/102632 | 8/2009 |
| WO | WO2011/090556 | 1/2010 |
| WO | WO2011/090557 | 1/2010 |
| WO | WO2011/090558 | 1/2010 |
| WO | WO-2010/033578 A2 | 3/2010 |
| WO | WO-2010/033578 A3 | 3/2010 |
| WO | WO-2012/027483 A2 | 3/2012 |
| WO | WO-2012/027483 A3 | 3/2012 |
| WO | WO-2014/180910 A1 | 1/2014 |
| WO | WO-2014/099919 A2 | 6/2014 |
| WO | WO-2014/099919 A3 | 6/2014 |

OTHER PUBLICATIONS

Enrich, et al., "Noninvasive detection of fetal trisomy 21 by sequencing of fetal DNA in maternal blood: a study in a clinical setting", Am J. Obstet Gynecol, 2011:204:205 e1-11 (2011).
Fan, et al., "Noninvasive diagnosis of fetal aneuploidy by shotgun sequencing DNA from maternal blood", PNAS USA, 105(42):16266-71 (2008).
Fan, et al., "Analysis of the Size Distributions of Fetal and Maternal Cell-Free DNA by Paired-End Sequencing", Clin. Chem., 56(8):1279-80 (2010).
Fan, et al., "Sensitivity of noninvasive prenatal detection of fetal aneuploidy from maternal plasma using shotgun sequencing is limited only by counting statistics", PLoS One, 5:e10439 (2010).
Fejgin, et al., "Fetal cells in the uterine cervix: a source for early non-invasive prenatal diagnosis", Prenat. Diag., 21:619-21 (2001).
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fournie, et al., "Plasma DNA as Cell Death Marker in Elderly Patients", Gerontology, 39:215-221 (1993).
Fowke, Genetic analysis of human DNA recovered from minute amounts of serum and plasma, J. of Immunol. Meth., 180:45-51 (1995).
Geifman-Holzman, et al., "Fetal RhD genotyping in fetal cells flow sorted from maternal blood", Am. J. Obstet. Gynecol., 174(3):818-22 (1996).
Ghossein, et al.. "Detection of Circulating Tumor Cells in Patients With Localized and Metastatic Prostate Carcinoma Clinical Implications", J. of Clin. Oncology, 13(5):1995-200 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Greeley, et al., "Get ready for the flood of fetal gene screening", Nature, 469:289-91 (2011).
Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Guatelli, et al., "Isothermal, in vitro amplification of nucleic acids by a multienzyme reaction modeled after retroviral replication", PNAS USA, 87(5):1874- (1990).
Han, et al, "Molecular Chytogenetic Characterization of 17 rob(13q14q) Robertsonian Translocations by FISH, Narrowing the Region Containing the Breakpoints", Am J. Hum. Genet., 55:960-67 (1994).
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Harrell, Regression modeling strategies, §§9.2.2 and 1.10.5 (Springer Vertag)(2001).
Heid, et al., "Real Time Quantitative PCR", Genome Res., 6:986-94 (1996).
Heilig, et al., "The DNA sequence and analysis of human chromosome 14", Nature, 421:601-09 (2003).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).
Hosny, et al., "TP53 mutations in circulating fee DNA from Egyptian patients with non-Hodgkin's lymphoma", Cancer Lett., 275(2):234-39 (2009).
International Human Genome Sequencing Consortium, "Initial sequencing and analysis of the human genome", Nature, 409:860-921 (2001).
Irizarry, et al., "Summaries of Affymetrix GeneChip probe level data", Nuc. Acid Res., 31(4):e5 (2003).
Kamnasaran and Cox, "Current status of chromosome 14", J. Med. Genet., 39:81-90 (2002).
Kazakov, et al., "Extracellular DNA in the Blood of Pregnant Women", Tsitologiia (Cytology), 37(3):232-37 (1995).
Kogan, et al., "An improved method for prenatal diagnosis of genetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Landegren, et al., "A ligase-mediated gene detection technique", Science, 241:1077 (1988).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).

(56) References Cited

OTHER PUBLICATIONS

Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", AM J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010).
Lo, "Fetal nucleic acids in maternal blood: the promises", Clin. Chem. Lab Med., 50(5):xxx-xxx (DOI 10.1515/CCLM.2011.765) (2011).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Abadia-Molina, et al., "Immune phenotype and cytotoxic activity of lymploycytes from human term decidua against trophoblast", J. of Reproductive Immunology, n31:109-23 (1996).
Agostini, et al., "Circulating cell-free DNA: a promising marker of pathologic tumor response in rectal cancer patients receiving pre-operative chemotherapy", Ann. Surg. Oncol., 18(9):2461-68 (2011).
Alexandrov, et al., "Definition of a new alpha satellite suprachromosomal family characterized by monomeric organization", Nucleic Acids Research, 21(9):2209-15 (2003).
Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63 (1979).
Ashoor, et al., Fetal Fraction in Maternal Plasma Cell-Free DNA at 11-13 Weeks' Gestation: Effect of Maternal and Fetal Factors, Fetal Dian Ther DOI:10.1159/000337373 (Pub'd online May 4, 2012).
Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029.
Arnheim, et al., "Molecular evidence for genetic exchanges among ribosomal genes on nonhomologous chromosomes in man and apes", PNAS USA, 77(12):7323-27 (1980).
Bandyopadhyay, et al, "Identification and characterization of satellite III subfamilies to the acrocentric chromosomes", Chromosome Research, 9:223-33 (2001).
Batzer and Deininger, "ALU Repeats and Human Genomic Diversity", Nature, 3:370-79 (2002).
Beard, "Embryological Aspects and Etiology of Carcinoma", The Lancet, Jun. 21, 1902, pp. 1758-1761.
Belokhvostov, et al., "Changes in the Fractional Composition of the Nucleic Acids in Blood Serum upon Rediation Damage Early Stage Abnormalities Following Gamma-Irradiation of Rats", Tsitologiia (Cytology) 1986.
Bianchi, "Prenatal diagnosis by analysis of fetal cells in maternal blood", J. of Pediatrics, 127(6):847-56 (1995).
Bianchi, "Isolation of fetal DNA from nucleated erythrocytes in maternal blood", PNAS USA, 87:3279-83 (1990).
Bianchi, "PCR Quantitation of Fetal Cells in Maternal Blood in Normal and Aneuploid Pregnancies", Am J. Hum. Genet., 61:822-29 (1997).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bodurtha and Strauss, "Genomics and Prenatal Care", New Eng. J. of Medicine, 366:64-73 (2012).
Bombard, et al., "Fetal RHD genotype detection from circulating cell-free DNA in maternal plasma in non-sensitized RhD negative women", Prenat Diagn, 31:802-08 (2011).
Bradstock, et al., "Functional and phenotypic assessment of neonatal human leucocytes expressing natural killer cell-associated antigen", Immunology and Cell Biology (71:535-42 (1993).
Camaschella, et al., "Prenatal Diagnosis of Fetal Hemoglobin Lepore-Boston Disease on Maternal Peripheral Blood", Blood, 75(11):2102-06 (1990).
Campbell, et al., "Subclonal phylogenetic structions in cancer revealed by ultra-deep sequencing", PNAS, 105(35):13081-86 (2008).
Cappuzzo, et al., "Epidermal growth factor receptor gene and protein and gefitinib sensitivity in non-small-cell lung cancer", J. Natl Cancer Inst., 97(9):643-55 (2005).
Cicuttini and Boyd, "Hemopoietic and Lymphoid Progenitro Cells in Human Umbilical Cord Blood", Developmental Immunology, 4:1-11 (1994).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011).
Chim, et al., "Detection of the placental epigenetic signature of the maspin gene in maternal plasma", PNAS USA, 102(41):14753-58 (2005).
Chiu, et al, "Effects of Blood-Processing Protocols on Fetal and Total DNA Quantification in Maternal Plasma", Clin. Chem., 47(9):1607-1613 (2001).
Chiu, et al., "Maternal plasma DNA analysis with massively parallel sequencing by ligation for noninvasive prenatal diagnosis of trisomy 21", 56:459-63 (2010).
Chiu, et al, "Noninvasive prenatal diagnosis of fetal chromosomal aneuploidy by massively parallel genomic sequencing of DNA in maternal plasma", PNAS USA 105:20458-63 (2008).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Non-invasive prenatal assessment of trisomy 21 by multiplexed maternal plasma DNA sequencing: large scale validity study", Br Med J. 342:c7401 (2011).
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Choo, et al., "A homologous subfamily of satellite III DNA on human chromosomes 14 and 22", Nucleic Acids Research, 18(19):5641-47 (1990).
Choo, et al., "A Chromosome 14-specific Human Satellite III DNA Subfamily That Shows Variable Presence on Different Chromosomes 14", Am J. Hum. Genet., 50:706-16 (1992).
Chromosome 14 map.
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).

(56) References Cited

OTHER PUBLICATIONS

Cockwell, et al., "Distribution of the D15A1 copy number polymorphism", European J. of Hum. Genet., 15:441-45 (2007).
Conover, Practical Nonparametric Statistics, pp. 295-01 (John Wiley & Sons, NY)(1971).
Costa, et al., "New strategy for prenatal diagnosis of X-linked disorders", N. Engl J. Med., 346:1502 (2002).
Datta, et al., "Sensitive Detection of Occult Breast Cancer by the Reverse-Transcriptase Polymerase Chain Reaction", J. of Clinical Oncology, 12(3): 475-82 (1994).
Dear, et al., "A High-Resolution Metric HAPPY Map of Human Chromosome 14" Genmoics, 48 232-41 (1998).
Dennin, "DNA of Free and Complexed Origin in Human Plasma: Concentration and Length Distribution", Klin. Wochenschr., 57:451-56 (1979).
Dhallan, et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer", Ginekol Pol. 81(6):422-25 (2010).
Sparks, et al., "Selective analysis of cell-free DNA in maternal blood for evaluation of fetal trisomy", Prenatal Diagnosis, 32:1-7 (2012).
Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030.
Stroun, et al., "Neoplastic Characteristics of the DNA Found in the Plasma of Cancer Patients", Oncology, 46: 318-322 (1989).
Stroun, et al., "Isolation and Characterization of DNA from the Plasma of Cancer Patients", Eur. J. Cancer Clin. Oncol., 23(6)707-12 (1987).
Stroun, et al., "Circulating Nulceic Acids in Higher Organisms", Rev. Cytol. 51:1-48 (1977).
Stroun, et al., The Origin and Mechanism of Circulating DNA, Annals New York Academy of Sciences, 906:161-68 (2000).
Sullivan, et al., "Evidence for Structural Heterogeneity from Molecular Cytogenetic Analysis of Dicentric Robertsonian Translocations", Am. J. Hum. Genet., 59:167-75 (1996).
Tagle, et al., "An optimized Alu-PCR primer pair for human-specific amplification of YACs and somatic cells hybrids", Human Molecular Genetics, 1(2):121-22 (1992).
Tomilin, et al., "Mechanisms of Chromosome Destabilization in Human Cells", Sov. Sci. Rev. D. Physiochem. Biol., 10:39-89 (1992).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Systematic microarray-based identification of placental mRNA in maternal plasma: towards non-invasive prenatal gene expression profiling", J. Med Genet, 41:461-67 (2004).
Tsui, et al., "Noninvasive prenatal diagnosis of hemophilia by microfluidics digital PCR analysis of maternal plasma DNA", Blood, 117:3684=91 (2011).
Ulbright, "Germ cell tumors of the gonads: a selective review emphasizing problems in differential diagnosis, newly appreciated, and controversial issues," Modern Pathology, 18:S61-S79 (2005).
Vasioukhin, et al., "Point mutations in the N-ras gene in the blood plasma DNA of patients with myelodysplastic cyndrome or acute myelogenous leukaemia", British J. of Haematology, 86:774-79 (1994).
Vogelstein, et al., "Digital PCR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10):1466-69 (1991).
Wald, et al., "Maternal serum screening for Down's syndrome in early pregnancy", BMJ, 297:883-87 (1988).
Wald, et al., "Antenatal maternal serum screening for Down's syndrome: results of a demonstration project", BMJ, 305(6850):391-94 (1992).
Walker, et al., "Human DNA quantitation using Alu element-based polymerase chain reaction", Analytical Biochem., 315:122-28 (2003).
Wang, et al., "PennCNV: An integrated hidden Markov model designed for high-resolution copy number variation detection in whole-genome SNP genotyping data", Genome Res., 17:1665-74 (2007).
Ward, et al., "Reactivities of serotyping monoclonal antibodies with culture-adapted human rotaviruses", J. Clin Microbiol. 29(3):422-25 (1991).
Winsor, et al., "Maternal Cell Contamination in Uncultured Amniotic Fluid", Prenatal Diagnosis, 16:49-54 (1996).
Witt, et al., "An improved, non-isotopic method of screening cells from patients with abnormalities of sexual differentiation for Y chromosomal DNA content", J. Med. Genet., 30:304-07 (1993).
Wu and Wallace, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Search Report for (PCT/US2012/21955).
Search Report for PCT/US2011/046935).
Search Report for (PCT/US2012/026754).
Search Report for (PCT/US2012/022261).
Search Report for (PCT/US2011/046976).
Search Report for (PCT/US2011/046981).
Office Action for U.S. Appl. No. 13/013,732.
Office Action for U.S. Appl. No. 13/293,419.
Enders, et al., "Fetal morbidity and mortality after acute human parvovirus B19 infection in pregnancy: prospective evaluation of 1018 cases", Prenatal Diagnosis, 24:513-18 (2004).
Smith, et al., "Quantitative phenotyping via deep barcode sequencing", Genome Res., 19:1836-42 (2009).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).
Xie and Tammi, "CNV-seq, a new method to detect copy number variation using high throughput sequencing", BMC Bioinformatics, 10:80 (2008), doi 10.1186/1471-2105-10-80, p. 1-9.
Office Action for U.S. Appl. No. 13/356,133, inventor A. Oliphant, filed Jan. 23, 2012, entire document.
Office Action for U.S. Appl. No. 13/356,575, inventor A. Oliphant, filed Jan. 23, 2012, entire document.
Office Action for U.S. Appl. No. 13/689,206, inventor A. Oliphant, filed Nov. 39, 2012.
Final Office Action for U.S. Appl. No. 13/689,206, inventor A. Oliphant, filed Nov. 39, 2012, entire document.
Office Action for U.S. Appl. No. 13/013,732, inventor A. Oliphant, filed Jun. 25, 2011.
Office Action for U.S. Appl. No. 13/013,732, inventor A. Oliphant, filed Jun. 25, 2011, entire document.
Office Action for U.S. Appl. No. 13/407,978, inventor K. Song, filed Feb. 29, 2012, entire document.
Office Action for U.S. Appl. No. 13/205,490, inventor A. Sparks, filed Aug. 8, 2011, entire document.
Office Action for U.S. Appl. No. 13/687,169, inventor A. Sparks, filed Nov. 28, 2012, entire document.
Office Action for U.S. Appl. No. 13/205,570, inventor A. Sparks, filed Aug. 8, 2011, entire document.
Office Action for U.S. Appl. No. 13/687,025, inventor A. Sparks, filed Nov. 28, 2012, entire document.
Office Action for U.S. Appl. No. 13/293,419, inventor A. Sparks, filed Nov. 10, 2011, entire document.
Final Office Action for U.S. Appl. No. 13/293,419, inventor A. Sparks, filed Nov. 10, 2011, entire document.
Advisory Action for U.S. Appl. No. 13/293,419, inventor A. Sparks, filed Nov. 10, 2011, entire document.

(56) References Cited

OTHER PUBLICATIONS

Office Action for U.S. Appl. No. 13/245,133, inventor A. Oliphant, filed Sep. 26, 2011, entire document.
Office Action for U.S. Appl. No. 13/316,154, inventor A. Oliphant, filed Dec. 9, 2011, entire document.
Office Action for U.S. Appl. No. 13/338,963, inventor A. Oliphant, filed Dec. 28, 2011, entire document.
Office Action for U.S. Appl. No. 13/689,417, inventor A. Oliphant, filed Nov. 29, 2012, entire document.
Search Report for (PCT/US2011/046963), entire document.
Search Report for (PCT/US2012/70177), entire document.
Bianchi, et al., "Large Amounts of Cell-free DNAs Are Present in Amniotic Fluid", Clin. Chem., 47(10) 1867-69 (2001).
Centre for Genomics Education, "Changes to Chromosome Structure—Translocations", The Australasian Genetics Resource Book, www.genetics.com, pp. 1-5 (2007).
Chiu, et al., "Non-invasive prenatal diagnosis by single molecule counting technologies", Trends in Genomics, 25(7):324-31 (2009).
Hayden, et al., "Multiplex-Ready PCR: A new method for multiplexed SSR and SNP genotyping", BMC Genomics, 9:80:1-12 (2007).
Hsuih, et al., "Novel, ligation-depdent PCR assay for detection of hepatitis C in serum", J. of Clin. Microbiology, 34(3):501-07 (1996).
Huang, et al., "Identification of a family of alternatively splied mRNA species of angiopoietin-1", Blood, 95:1993-99 (2000).
Indolfi, et al., "Perinatal Transmission of Hepatitis C Virus Infection", J. Med. Virol., 81:836-43 (2009).
Mardis, et al., "The impact of next-generation sequencing technology on genetics", Trends in Genetics, 24(3):133-41 (2007).
Porreca, et al., "Multiplex amplification of large sets of human exons", Nat. Methods, 4(11):931-36 (2007).
Schouten, et al., "Relative quantification of 40 nucleic acid sequences by multiplex ligation-dependent probe amplification", Nuc. Ac. Res., 30(12):e57 (2002).
Tewhey, et al., "Microdroplet-based PCR enrichment for large-scale targeted sequencing", Nat. Biotech., 27(11):1025-31 (2009).
Zolotukhina, et al., "Analysis of Cell-free DNA in Plasma and Serum of Pregnant Women", J. of Hist. and Cytochem., 53:297-99 (2005).
Office Action for U.S. Appl. No. 13/356,575 filed Jan. 23, 2012, inventor Oliphant, entire document.
Office Action for U.S. Appl. No. 13/689,206, filed Nov. 29, 2012, inventor Oliphant, entire document.
Office Action for U.S. Appl. No. 13/356,133, filed Jan. 23, 2012, inventor Oliphant, entire document.
Office Action for U.S. Appl. No. 13/013,732, filed Jun. 25, 2011, inventor Oliphant, entire document.
Office Action for U.S. Appl. No. 13/405,839, filed Feb. 27, 2012, inventor Oliphant, entire document.
Office Action for U.S. Appl. No. 13/407,978, filed Feb. 29, 2012, inventor Song, entire document.
Office Action for U.S. Appl. No. 13/605,505, filed Sep. 6, 2012, inventor Struble, entire document.
Office Action for U.S. Appl. No. 13/687,169, filed Nov. 28, 2012, inventor Sparks, entire document.
Office Action for U.S. Appl. No. 13/205,490, filed Aug. 8, 2011, inventor Sparks, entire document.
Office Action for U.S. Appl. No. 13/687,025, filed Nov. 28, 2012, inventor Sparks, entire document.
Office Action for U.S. Appl. No. 13/687,025, filed Nov. 28, 2011, inventor Sparks, entire document.
Office Action for U.S. Appl. No. 13/205,570, filed Aug. 8, 2011, inventor Sparks, entire document.
Office Action for U.S. Appl. No. 13/293,419, filed Nov. 10, 2011, Sparks, entire document.
Office Action for U.S. Appl. No. 13/205,603, filed Aug. 8, 2011, inventor Sparks, entire document.
Office Action for U.S. Appl. No. 13/274,309, filed Oct. 15, 2011, inventor Struble, entire document.
Office Action for U.S. Appl. No. 13/245,133, filed Sep. 26, 2011, inventor Oliphant, entire document.
Office Action for U.S. Appl. No. 13/689,417, filed Nov. 29, 2012, inventor Oliphant, entire document.
Office Action, filed Dec. 9, 2011, inventor Oliphant for U.S. Appl. No. 13/316,154, entire document.
Australian Patent Examination Report No. 1 dated Feb. 20, 2014 for 2011285512, entire document.
Australian Patent Examination Report No. 1 dated Mar. 4, 2014 for 2011285518, entire document.
Australian Patent Examination Report No. 1 dated Feb. 7, 2014 for 2011285477, entire document.
EPO Examination Report dated Nov. 21, 2013 for App. No. 11745880.2, entire document.
EPO Examination Report dated Nov. 21, 2013 for App. No. 11745881.1, entire document.
EPO Examination Report dated Nov. 28, 2013 for App. No. 11745883.6, entire document.
Search Report dated Sep. 12, 2013 for PCT/US 2012/026754, entire document.
Search Report dated Nov. 15, 2013 for PCT/US 2013/51310, entire document.
Search Report dated May 14, 2013 for PCT/US 2014/17092, entire document.
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Margulies, et al., "Genome sequencing in microfabricated high-density picolitre reactors", Nature, 437(15):376-80 and errata (2005).
Mikhaylov, et al., "Changes in the quantity and synthesis of DNA in the nuclei of large decidual cells of rats in the course of their differentiation", Tsitologiia (Cytology),41(6):677-83.
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.
Moreno and Gomella, "Circulating Prostate Cancer Cells Detected by Reverse Transcription-Polymerase Chain Reaction (RT-PCR: What do they mean?", Cancer Control Journal, 5(6).
Mulcahy, et al., "Plasma DNA K-rase Mutations in Patients with Gastrointestinal Malignancies," Annals New York Academy of Sciences, 25-28.
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz, et al., "Microsatellite alterations in serum DNA of head and neck cancer patients", Nature Medicine, 2(9):1035-37 (1996).
Nelson, et al., "Alu polymerase chain reaction: A method for rapid isolation of human-specific sequence from complex DNA sources," PNAS USA, 86:6686-90 (1989).
Ng, et al., "mRNA of placental origin is readily detectable in maternal plasma", PNAS USA, 100:4748-53 (2003).
Oei, et al., "Clusters of regulatory signals for RNA polymerase II transcription associated with Alu family repeats and CpG islands in human promoters", Genomics, 83:873-82 (2004).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Paolella, et al., "The Alu family repeat promoter has a tRNA-like bipartite structure", EMBO J., 2(5):691-96 (1983).

(56) References Cited

OTHER PUBLICATIONS

Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Robbins, et al., *Pathologic Basis of Disease 5th Ed.*, Chapter 23, pp. 1071-1088 (1994).
Ronaghi, et al., "A Sequencing Method Based on Real_Time Pyrophosphate", Science, 281:363-65 (1998).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Saiki, et al., "Primer-directed Enzymatic Amplification of DNA with a Thermostable DNA Polymerase", Science, 239:487-91 (1987).
Savas, "Useful genetic variation databases for oncologists investigating the genetic basis of variable treatment response and survival in cancer", Acta Oncol., 49(8):1217-26 (2010).
Shendure, et al., "Accurate Multiplex Polony Sequencing of an Evolved Bacterial Genome", Science, 309:1728-32 (2005).
Schallhammer, et al., "Phenotypic comparison of natural killer cells from peripheral blood and from early pregnancy decidua", Early Pregnancy: Biology and Medicine, 3:15-22 (1997).
Schroder, et al., "Transplacental passage of blood cells", J. of Medical Genetics, 12:230-42 (1974).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Shapiro, et al., "Determination of Circulating DNA Levels in Patients with Benign or Malignant Gastrointestinal Disease", Cancer, 51:2116-20 (1983).
Simpson and Elias, "Isolating Fetal Cells from Maternal Blood", JAMA, 270(19):2357-61 (1993).
Simpson, et al., "Isolating Fetal Cells in Maternal Circulation for Prenatal Diagnosis", Prenatal Diagnosis, 14:1229-42 (1994).
Simpson, "Is Cell-Free Fetal DNA from Maternal Blood Finally Ready for Prime Time?", Obst & Gynecol., 119(5):1-3 (2012).
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3_67-71 (1994).
Smith, et al.,"Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Sorenson, et al., "Soluble normal and mutated DNA sequences from single-copy genes in human blood", Cancer Epidemmiol. Biomarkers, 3:64-71 (1994).
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.
Donnenfeld, A. et al. (Dec. 1, 2001). "Biochemical Screening for Aneuploidy in Ovum Donor Pregancies," *Am J Obstet Gynecol* SMFM Abstracts S221, 1 page.
European Search Report dated Jul. 18, 2016 for EP Application No. 13864118.8, filed Dec. 17, 2013, 7 pages.
Keskintepe, L. et al. (Sep. 2007). "Reproductive oocyte/embryo genetic analysis: comparison between fluorescence in-situ hybridization and comparative genomic hybridization," *Reprod Biomed Online* 15(3):303-309.
Sparks, A. et al. (2012). "Non-Invasive Prenatal testing: A New Era in Fetal Trisomy Detection," *American Journal of Obstetrics & Gynecology* 206(4): Supplementary materials, 25 pages.
Donnenfeld, A. et al. (Dec. 1 , 2001), "Biochemical Screening for Aneuploidy in Ovum Donor Pregancies," *Am J Obstet Gynecol* 187(5):1222-1225.
Tewhey, R. et al. (2009, e-published Nov. 1, 2009). "Microdroplet-based PCR enrichment for large-scale targeted sequencing," *Nat Biotechnol* 27(11):1025-1031; Supplementary materials: 33 pages.

* cited by examiner

| Combination # | Maternal Genotype | Egg Donor Genotype | Fetal Genotype | Informative? |
|---|---|---|---|---|
| 201 | AA | AA | AA | NO |
| 202 | AA | AA | AB | YES |
| 203 | AA | AB | AA | NO |
| 204 | AA | AB | AB | YES |
| 205 | AA | AB | BB | YES |
| 206 | AA | BB | AB | YES |
| 207 | AA | BB | BB | YES |
| 208 | AB | AA | AA | YES |
| 209 | AB | AA | AB | NO |
| 210 | AB | AB | AA | YES |
| 211 | AB | AB | AB | NO |
| 212 | AB | AB | BB | YES |
| 213 | AB | BB | AB | NO |
| 214 | AB | BB | BB | YES |

FIG. 2

NONINVASIVE DETECTION OF FETAL ANEUPLOIDY IN EGG DONOR PREGNANCIES

CROSS-REFERENCE TO RELATED APPLICATIONS

This application is a Continuation-In-Part of U.S. patent application Ser. No. 13/338,963, filed Dec. 28, 2011, which is a Continuation-In-Part of U.S. patent application Ser. No. 13/316,154, filed Dec. 9, 2011, which claims priority to U.S. Provisional Patent Application No. 61/436,135, filed Jan. 25, 2011, all of which are assigned to the assignee of the present invention and incorporated herein by reference.

FIELD OF THE INVENTION

This invention relates to diagnosis of genetic abnormalities in egg donor pregnancies and assay systems for such diagnosis.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genetic abnormalities account for a wide number of pathologies, including pathologies caused by chromosomal aneuploidy (e.g., Down syndrome), germline mutations in specific genes (e.g., sickle cell anemia), and pathologies caused by somatic mutations (e.g., cancer). Diagnostic methods for determining such genetic anomalies have become standard techniques for identifying specific diseases and disorders, as well as providing valuable information on disease source and treatment options.

For example, prenatal screening and diagnosis are routinely offered in antenatal care and are considered to be important in allowing women to make informed choices about pregnancies affected by genetic conditions. Conventional methods of prenatal diagnostic testing currently requires removal of a sample of fetal cells directly from the uterus for genetic analysis, using either chorionic villus sampling (CVS) typically between 11 and 14 weeks gestation or amniocentesis typically after 15 weeks. However, these invasive procedures carry a risk of miscarriage of around 1%. Mujezinovic and Alfirevic, Obstet Gynecol 2007; 110:687-694.

Although these approaches to obtaining fetal DNA currently provide the gold standard test for prenatal diagnosis, many women decide not to undergo invasive testing, primarily because it is unpleasant and carries a small but significant risk of miscarriage. A reliable and convenient method for non-invasive prenatal diagnosis has long been sought to reduce this risk of miscarriage and allow earlier testing. Although some work has investigated using fetal cells obtained from the cervical mucus (Fejgin M D et al. Prenat Diagn 2001; 21:619-621; Mantzaris et al., ANZJOG 2005; 45:529-532), most research has focused on strategies for detecting genetic elements from the fetus present in the maternal circulation. It has been demonstrated that there is bidirectional traffic between the fetus and the mother during pregnancy (Lo et al., Blood 1996; 88:4390-4395), and multiple studies have shown that both intact fetal cells and cell-free fetal nucleic acids cross the placenta and circulate in the maternal bloodstream (See, e.g., Chiu R W and Lo Y M, Semin Fetal Neonatal Med. 2010 Nov. 11).

In particular, more recent attempts to identify aneuploidies have used maternal blood as a starting material. Such efforts have included the use of cell-free DNA to detect fetal aneuploidy in a sample from a pregnant female, including use of massively parallel shotgun sequencing (MPSS) to quantify precisely the increase in cfDNA fragments from trisomic chromosomes. The chromosomal dosage resulting from fetal aneuploidy, however, is directly related to the fraction of fetal cfDNA. Variation of fetal nucleic acid contribution between samples can thus complicate the analysis, as the level of fetal contribution to a maternal sample will vary the amounts needed to be detected for calculating the risk that a fetal chromosome is aneuploid.

For example, a cfDNA sample containing 4% DNA from a fetus with trisomy 21 should exhibit a 2% increase in the proportion of reads from chromosome 21 (chr21) as compared to a normal fetus. Distinguishing a trisomy 21 from a normal fetus with high confidence using a maternal sample with a fetal nucleic acid percentage of 4% requires a large number (>93K) of chromosome 21 observations, which is challenging and not cost-effective using non-selective techniques such as MPSS.

There is thus a need for non-invasive methods of screening for genetic abnormalities, including aneuploidies, in mixed samples comprising normal and putative abnormal DNA. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides assay systems and related methods for determining genetic abnormalities in maternal samples comprising genomic material (e.g., cell-free DNA) in egg donor pregnancies. The analysis for determination of fetal aneuploidy can be performed using various techniques.

Determining the relative percentage of fetal DNA in a maternal sample from an egg donor pregnancy provides important information on the relative statistical presence of nucleic acid regions that may be indicative of fetal aneuploidy. Determining the loci in which the fetus has at least one allele that is different from the alleles of the carrier can allow the estimation of fetal DNA in a maternal sample, and thus provide information used to calculate the statistically significant differences in chromosomal frequencies for chromosomes of interest. Such loci could thus provide two forms of information in the assay—allelic information can be used for determining the percent fetal DNA contribution in the maternal sample and empirical determination of the allelic information from the detection techniques (e.g. summation of the allelic detection levels) can be used to determine the relative overall frequency of that locus in a maternal sample. The allelic information, however, is not needed to determine the relative overall frequency of that locus.

Thus, in some specific aspects, the relative fetal contribution of maternal DNA at the allele of interest can be compared to the non-maternal contribution at that allele to determine approximate fetal DNA concentration in the sample. In a particular aspect, the estimation of fetal DNA in a maternal sample is determined at those loci where the fetal DNA has at least one allele that is different from the maternal alleles. In an egg donor pregnancy, this may include loci in which either the maternal or fetal genotype is homozygous and the other is heterozygous and loci in which both the maternal and fetal genotypes are homozygous, and both fetal alleles are different from the maternal alleles. In this situation, the fetal DNA amount may be determined using a subset of egg donor informative loci.

In one specific aspect, the invention provides a method for determining the percent fetal cell-free DNA in a maternal sample from a pregnant female with an egg donor pregnancy comprising providing a maternal sample comprising maternal and fetal cell-free DNA; interrogating two or more selected polymorphic nucleic acid regions; detecting the interrogated nucleic acid regions; determining a relative frequency of polymorphisms in the interrogated nucleic acid regions to identify egg donor informative loci; calculating a percent fetal cell-free DNA using the identified egg donor informative loci.

In certain specific aspects, determining the relative percentage of fetal DNA in a maternal sample may be beneficial in performing or optimizing results obtained from the assay system, as it will provide important information on the expected statistical presence of the fetal chromosomes and deviation from that expectation may be indicative of fetal aneuploidy. Numerous approaches can be used to calculate the relative contribution of fetal DNA in a maternal sample.

In one specific aspect, the invention provides an assay system for providing a statistical likelihood of the presence or absence of fetal aneuploidy in a pregnant female with an egg donor pregnancy, comprising providing a maternal sample comprising maternal and fetal cell-free DNA; interrogating two or more nucleic acid regions from a first chromosome; quantifying a relative frequency of alleles from the nucleic acid regions from the first chromosome; interrogating two or more selected nucleic acid regions from a second chromosome; comparing the relative frequency of the nucleic acid regions from the first chromosome to the relative frequency of the nucleic acid regions form the second chromosome; calculating percent fetal cell-free DNA in the maternal sample; and providing a statistical likelihood of the presence of absence of a fetal aneuploidy using the calculated percent fetal cell-free DNA in the maternal sample.

In one specific aspect, the invention provides an assay system for providing a statistical likelihood of the presence or absence of fetal aneuploidy in a pregnant female with an egg donor pregnancy, comprising providing a maternal sample comprising maternal and fetal cell-free DNA; interrogating two or more nucleic acid regions from a first chromosome; detecting the interrogated nucleic acid regions from the first chromosome; quantifying a relative frequency of alleles from the nucleic acid regions from the first chromosome; interrogating two or more selected nucleic acid regions from a second chromosome; detecting the interrogated nucleic acid regions from the second chromosome; quantifying a relative frequency of alleles from the nucleic acid regions from the second chromosome; comparing the relative frequency of the nucleic acid regions from the first chromosome to the relative frequency of the nucleic acid regions form the second chromosome; calculating percent fetal cell-free DNA in the maternal sample; and providing a statistical likelihood of the presence of absence of a fetal aneuploidy using the calculated percent fetal cell-free DNA in the maternal sample.

In one specific aspect, the invention provides an assay system for providing a statistical likelihood of the presence or absence of fetal aneuploidy in a pregnant female with an egg donor pregnancy, comprising providing a maternal sample comprising maternal and fetal cell-free DNA; interrogating two or more nucleic acid regions from a first chromosome; quantifying a relative frequency of alleles from the nucleic acid regions from the first chromosome; interrogating two or more selected nucleic acid regions from a second chromosome; quantifying a relative frequency of alleles from the nucleic acid regions from the second chromosome; comparing the relative frequency of the nucleic acid regions from the first chromosome to the relative frequency of the nucleic acid regions form the second chromosome; calculating percent fetal cell-free DNA in the maternal sample; and providing a statistical likelihood of the presence of absence of a fetal aneuploidy using the calculated percent fetal cell-free DNA in the maternal sample.

In some aspects, the percent fetal DNA contribution in a maternal sample is calculated by determining levels of one or more non-maternally contributed loci, including loci on the sex chromosomes and autosomal loci. In aspects utilizing autosomal loci, generally the percent fetal DNA contribution is determined by comparing one or more genetic variations on the non-maternal loci to the maternal loci. In some particular aspects, these genetic variations are copy number variations. In other particular aspects, these genetic variations are one or more single nucleotide polymorphisms.

The assay system preferably analyzes at least ten polymorphic nucleic acid regions for each chromosome of interest, more preferably at least twenty polymorphic nucleic acid regions for each chromosome of interest, more preferably at least forty polymorphic nucleic acid regions for each chromosome of interest, and even more preferably at least ninety polymorphic nucleic acid regions for each chromosome of interest.

The assay system of the invention can be configured as a highly multiplexed system which allows for multiple nucleic acid regions from a single or multiple chromosomes within an individual sample and/or multiple samples to be analyzed simultaneously. In such multiplexed systems, the samples can be analyzed separately, or they may be initially pooled into groups of two or more for analysis of larger numbers of samples. When pooled data is obtained, such data is preferably identified for the different samples prior to analysis of aneuploidy. In some aspects, however, the pooled data may be analyzed for potential aneuploidies, and individual samples from the group subsequently analyzed if initial results indicate that a potential aneuploidy is detected within the pooled group.

In certain aspects, the assay systems utilize one or more indices that provide information for sample or locus identification. For example, a primer that is used in selective amplification may have additional sequences that are specific to a locus, e.g., a nucleic acid sequence that is indicative of the selected nucleic acid region or a particular allele of that nucleic acid region. In another example, an index is used in selective or universal amplification that is indicative of a sample from which the nucleic acid was amplified. In yet another example, a unique identification index is used to distinguish a particular amplification product from other amplification products obtained from the detection methods. A single index may also be combined with any other index to create one index that provides information for two properties (e.g., sample-identification index, allele-locus index).

In certain aspects, the nucleic acid regions are amplified using universal amplification methods. Universal amplification can be done, for example, after an initial selective amplification or enrichment step from the maternal sample from an egg donor pregnancy. The use of universal amplification allows multiple nucleic acid regions to be amplified using a single or limited number of amplification primers, and is especially useful in amplifying multiple selected nucleic acid regions in a single reaction. This allows the simultaneous processing of multiple nucleic acid regions from a single or multiple samples.

The maternal sample used for analysis can be obtained or derived from any pregnant woman with an egg donor pregnancy. For example, a maternal sample may be from any maternal fluid which comprises both maternal and fetal cell-free DNA, including but not limited to maternal plasma, maternal serum, or maternal blood.

In preferred aspects, target nucleic acids corresponding to multiple nucleic acid regions from a chromosome are detected and frequency used to determine the relative frequency of a chromosome in the maternal sample. Frequencies that are higher than expected for a nucleic acid region corresponding to one chromosome when compared to the quantity of a nucleic acid region corresponding to another chromosome in the maternal sample are indicative of a fetal duplication, deletion or aneuploidy. The comparison can be comparison of a genomic region of interest that is putatively inserted or deleted in a fetal chromosome. The comparison can also be of chromosomes that each may be a putative aneuploid in the fetus (e.g., chromosomes 18 and 21), where the likelihood of both being aneuploid is minimal. The comparison can also be of chromosomes where one is putatively aneuploid (e.g., chromosome 21) and the other acts as a reference chromosome (e.g., an autosome such as chromosome 12). In yet other aspects, the comparison may utilize two or more chromosomes that are putatively aneuploid and one or more reference chromosomes.

These and other aspects, features and advantages will be provided in more detail as described herein.

BRIEF DESCRIPTION OF THE FIGURES

FIG. 2 is a table of combinations of maternal, egg donor, and fetal genotypes in an egg donor pregnancy at a particular locus.

DETAILED DESCRIPTION OF THE INVENTION

Figure 1:
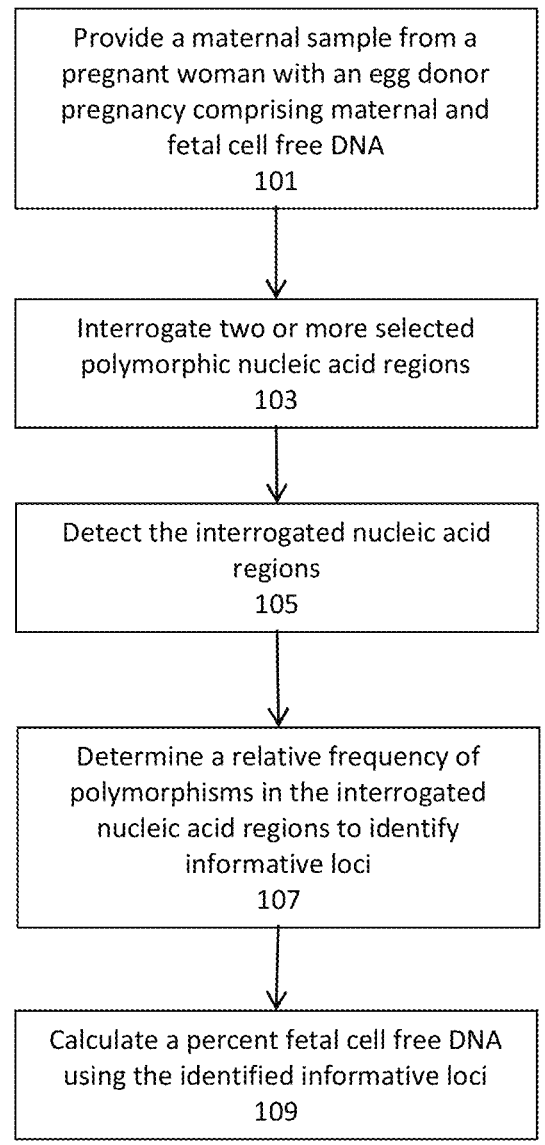
FIG. 1 is a simplified flow chart of the general steps for determination of percent fetal contribution of cell-free DNA in a maternal sample.

The methods described herein may employ, unless otherwise indicated, conventional techniques and descriptions of molecular biology (including recombinant techniques), cell biology, biochemistry, and microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Gait, "Oligonucleotide Synthesis: A Practical Approach" IRL Press, London (1984); Nelson and Cox, *Lehninger, Principles of Biochemistry*, $3^{rd}$ Ed., W. H. Freeman Pub., New York (2000); and Berg et al., *Biochemistry*, $5^{th}$ Ed., W.H. Freeman Pub., New York (2002), all of which are herein incorporated by reference in their entirety for all purposes.

Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "and," and "the" include plural referents unless the context clearly dictates otherwise. Thus, for example, reference to "a nucleic acid region" refers to one, more than one, or mixtures of such regions, and reference to "an assay" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

All publications mentioned herein are incorporated by reference for the purpose of describing and disclosing the formulations and methodologies that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Definitions

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication method performed in vitro as compared to its starting amount.

The term "carrier mother" refers to a pregnant woman who carries a fetus resulting from the use of a human oocyte that is from a different woman.

The term "chromosomal abnormality" refers to any genetic variant for all or part of a chromosome. The genetic variants may include but not be limited to any copy number variant such as duplications or deletions, translocations, inversions, and mutations.

The terms "complementary" or "complementarity" are used in reference to nucleic acid molecules (i.e., a sequence of nucleotides) that are related by base-pairing rules. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100% complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Stringent hybridization conditions will typically include salt concentrations of less than about 1 M, more usually less than about 500 mM and preferably less than about 200 mM. Hybridization temperatures are generally at least about 2° C. to about 6° C. lower than melting temperatures ($T_m$).

The term "correction index" refers to an index that may contain additional nucleotides that allow for identification and correction of amplification, sequencing or other experimental errors including the detection of deletion, substitution, or insertion of one or more bases during sequencing as well as nucleotide changes that may occur outside of sequencing such as oligo synthesis, amplification, and any other aspect of the assay. These correction indices may be stand-alone indices that are separate sequences, or they may be embedded within other indices to assist in confirming accuracy of the experimental techniques used, e.g., a correction index may be a subset of sequences of a locus index or an identification index.

The term "diagnostic tool" as used herein refers to any composition or assay of the invention used in combination as, for example, in a system in order to carry out a diagnostic test or assay on a patient sample.

The term "egg donor pregnancy" refers to a pregnancy resulting from the use of a human oocyte that is not from the carrier mother.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The term "identification index" refers generally to a series of nucleotides incorporated into a primer region of an amplification process for unique identification of an amplification product of a nucleic acid region. Identification index sequences are preferably 6 or more nucleotides in length. In a preferred aspect, the identification index is long enough to have statistical probability of labeling each molecule with a target sequence uniquely. For example, if there are 3000 copies of a particular target sequence, there are substantially more than 3000 identification indexes such that each copy of a particular target sequence is likely to be labeled with a unique identification index. The identification index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay. The index may be combined with any other index to create one index that provides information for two properties (e.g., sample-identification index, locus-identification index).

The term "likelihood" refers to any value achieved by directly calculating likelihood or any value that can be correlated to or otherwise indicative of a likelihood.

The terms "locus" and "loci" as used herein refer to a nucleic acid region of known location in a genome.

The term "locus index" refers generally to a series of nucleotides that correspond to a known locus on a chromosome. Generally, the locus index is long enough to label each known locus region uniquely. For instance, if the method uses 192 known locus regions corresponding to 192 individual sequences associated with the known loci, there are at least 192 unique locus indexes, each uniquely identifying a region indicative of a particular locus on a chromosome. The locus indices used in the methods of the invention may be indicative of different loci on a single chromosome as well as known loci present on different chromosomes within a sample. The locus index may contain additional nucleotides that allow for identification and correction of sequencing errors including the detection of deletion, substitution, or insertion of one or more bases during sequencing as well as nucleotide changes that may occur outside of sequencing such as oligo synthesis, amplification, and any other aspect of the assay.

The term "maternal sample" as used herein refers to any sample taken from a pregnant mammal which comprises both fetal and maternal cell free genomic material (e.g., DNA). Preferably, maternal samples for use in the invention are obtained through relatively non-invasive means, e.g., phlebotomy or other standard techniques for extracting peripheral samples from a subject.

The term "melting temperature" or $T_m$ is commonly defined as the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+16.6(\log 10[Na+]) 0.41(\%[G+C])-675/n-1.0$ m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual*, 3rd Ed., Cold Spring Harbor Laboratory Press (2001)). Other references include more sophisticated computations, which take structural as well as sequence characteristics into account for the calculation of $T_m$.

"Microarray" or "array" refers to a solid phase support having a surface, preferably but not exclusively a planar or substantially planar surface, which carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., *Microarrays: A Practical Approach*, IRL Press, Oxford (2000). "Array analysis", "analysis by array" or "analysis by microarray" refers to analysis, such as, e.g., isolation of specific nucleic acids or sequence analysis of one or more biological molecules using a microarray.

By "non-polymorphic", when used with respect to detection of selected nucleic acid regions, is meant a detection of such nucleic acid region, which may contain one or more polymorphisms, but in which the detection is not reliant on detection of the specific polymorphism within the region. Thus a selected nucleic acid region may contain a polymorphism, but detection of the region using the assay system of the invention is based on occurrence of the region rather than the presence or absence of a particular polymorphism in that region.

As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

According to the present invention, a "nucleotide" may be unlabeled or detectably labeled by well known techniques. Fluorescent labels and their attachment to oligonucleotides are described in many reviews, including Haugland, *Handbook of Fluorescent Probes and Research Chemicals*, 9th Ed., Molecular Probes, Inc., Eugene Oreg. (2002); Keller and Manak, *DNA Probes*, 2nd Ed., Stockton Press, New York (1993); Eckstein, Ed., *Oligonucleotides and Analogues: A Practical Approach*, IRL Press, Oxford (1991); Wetmur, *Critical Reviews in Biochemistry and Molecular Biology*, 26:227-259 (1991); and the like. Other methodologies applicable to the invention are disclosed in the following sample of references: Fung et al., U.S. Pat. No. 4,757,141; Hobbs, Jr., et al., U.S. Pat. No. 5,151,507; Cruickshank, U.S. Pat. No. 5,091,519; Menchen et al., U.S. Pat. No. 5,188,934; Begot et al., U.S. Pat. No. 5,366,860; Lee et al., U.S. Pat. No. 5,847,162; Khanna et al., U.S. Pat. No. 4,318,846; Lee et al., U.S. Pat. No. 5,800,996; Lee et al., U.S. Pat. No. 5,066,580; Mathies et al., U.S. Pat. No. 5,688,648; and the like. Labeling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4' dimethylaminophenylazo)benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides include [R6G]dUTP, [TAMRA]dUTP, [R110]dCTP, [R6G]dCTP, [TAMRA] dCTP, [JOE]ddATP, [R6G]ddATP, [FAM]ddCTP, [R110] ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink FluorX-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosomee Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg.

The terms "oligonucleotides" or "oligos" as used herein refer to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more. Suitable nucleic acid molecules may be prepared by the phosphoramidite method described by Beaucage and Carruthers (Tetrahedron Lett., 22:1859-1862 (1981)), or by the triester method according to Matteucci, et al. (J. Am. Chem. Soc., 103:3185 (1981)), both incorporated herein by reference, or by other chemical methods such as using a commercial automated oligonucleotide synthesizer.

As used herein the term "polymerase" refers to an enzyme that links individual nucleotides together into a long strand, using another strand as a template. There are two general types of polymerase—DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification methods may be used as an alternative to PCR.

The term "polymorphism" as used herein refers to any genetic changes in a locus that may be indicative of that particular locus, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a nucleic acid region to a capture oligonucleoitide for detection of a specific nucleic acid region.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "sample index" refers generally to a series of unique nucleotides (i.e., each sample index is unique to a sample in a multiplexed assay system for analysis of multiple samples). The sample index can thus be used to assist in nucleic acid region identification for multiplexing of different samples in a single reaction vessel, such that each sample can be identified based on its sample index. In a preferred aspect, there is a unique sample index for each sample in a set of samples, and the samples are pooled during sequencing. For example, if twelve samples are pooled into a single sequencing reaction, there are at least twelve unique sample indexes such that each sample is labeled uniquely. The index may be combined with any other index to create one index that provides information for two properties (e.g., sample-identification index, sample-locus index).

The term "selected nucleic acid region" as used herein refers to a nucleic acid region corresponding to an individual chromosome. Such selected nucleic acid regions may be directly isolated and enriched from the sample for detection, e.g., based on hybridization and/or other sequence-based techniques, or they may be amplified using the sample as a template prior to detection of the sequence. Nucleic acids regions for use in the assay systems of the present invention may be selected on the basis of DNA level variation between individuals, based upon specificity for a particular chromosome, based on CG content and/or required amplification conditions of the selected nucleic acid regions, or other characteristics that will be apparent to one skilled in the art upon reading the present disclosure.

The term "selective amplification", "selectively amplify" and the like refers to an amplification procedure that depends in whole or in part on hybridization of an oligo to a sequence in a selected genomic region. In certain selective amplifications, the primers used for amplification are complementary to a selected genomic region. In other selective amplifications, the primers used for amplification are universal primers, but they only result in a product if a region of the nucleic acid used for amplification is complementary to a genomic region of interest.

The terms "sequencing", "sequence determination" and the like as used herein refers generally to any and all biochemical methods that may be used to determine the order of nucleotide bases in a nucleic acid.

The term "specifically binds", "specific binding" and the like as used herein, when referring to a binding partner (e.g., a nucleic acid probe or primer, antibody, etc.) that results in the generation of a statistically significant positive signal under the designated assay conditions. Typically the interaction will subsequently result in a detectable signal that is at least twice the standard deviation of any signal generated as a result of undesired interactions (background).

The term "universal" when used to describe an amplification procedure refers to the use of a single primer or set of primers for a plurality of amplification reactions. For example, in the detection of 96 different target sequences, all the templates may share the identical universal priming sequences, allowing for the multiplex amplification of the 96 different sequences using a single set of primers. The use of such primers greatly simplifies multiplexing in that only two primers are needed to amplify a plurality of selected nucleic acid sequences. The term "universal" when used to describe a priming site is a site to which a universal primer will hybridize.

It should also be noted that "sets" of universal priming sequences/primers may be used. For example, in highly multiplexed reactions, it may be useful to use several sets of universal sequences, rather than a single set; for example, 96 different nucleic acids may have a first set of universal priming sequences, and the second 96 a different set of universal priming sequences, etc.

The Invention in General

The present invention provides improved methods for identifying copy number variants of particular genomic regions, including complete chromosomes (e.g., aneuploidies), in mixed samples comprising cell-free DNA of pregnant woman with an egg donor pregnancy. These methods are useful for any mixed sample from an individual comprising cell free genomic material (e.g., DNA) from two or more distinct individuals, e.g., mixed samples comprising maternal and fetal cell-free DNA, mixed samples comprising cell-free DNA from a transplant donor and recipient, and the like.

In certain aspects, percent fetal contribution in a maternal sample from an egg donor pregnancy is estimated using the assay methods of the present invention. In certain specific aspects and as described herein, determining the percentage fetal contribution of cell-free DNA in a maternal sample can be used to increase the accuracy of frequency calculations for the selected nucleic acid regions used in determining a likelihood of the presence or absence of fetal aneuploidy.

In certain aspects, the assay methods of the invention provide a selected enrichment of nucleic acid regions from chromosomes of interest and/or reference chromosomes for copy number variant detection. A distinct advantage of the invention is that the selected nucleic acid regions can be further analyzed using a variety of detection and quantification techniques, including but not limited to hybridization techniques, digital PCR and high throughput sequencing determination techniques. Selection probes can be designed against any number of nucleic acid regions for any chromosome. Although amplification prior to the identification and quantification of the selection nucleic acids regions is not mandatory, limited amplification prior to detection is preferred.

Determination of Fetal DNA Content in Maternal Sample

The present invention provides methods for identifying fetal chromosomal aneuploidies in maternal samples comprising both maternal cell-free DNA from a carrier mother and fetal cell-free DNA in an egg donor pregnancy and assay systems for such identification. In certain aspects, determining the relative percentage of fetal DNA in a maternal sample may be beneficial in performing the assay system, as it will provide important information on the expected statistical presence of genomic regions and variation from that expectation may be indicative of copy number variation associated with insertion, deletions or aneuploidy. This may be especially helpful in circumstances where the level of fetal DNA in a maternal sample is low, as the percent fetal contribution can be used in determining the quantitative statistical significance in the variations of levels of identified nucleic acid regions in a maternal sample. In other aspects, the determination of the relative percent fetal cell-free DNA in a maternal sample may be beneficial in estimating the level of certainty or power in detecting a fetal aneuploidy. Inaccurate estimation of percent fetal cell-free DNA contribution can cause inaccurate risk determination of the presence or absence of fetal aneuploidy, leading to a false positive or a false negative result.

The methods of the invention include interrogation of egg donor informative loci in selected nucleic acid regions which are then detected to determine a relative frequency of alleles to identify egg donor informative loci such as low frequency alleles and high frequency alleles. High frequency alleles are maternal alleles, whether or not those alleles are present in the fetal genome, since maternal alleles are naturally in greater abundance in the maternal sample. Low frequency alleles are fetal alleles where at least one copy of the allele is absent from the maternal genome. Frequency of the low frequency alleles and frequency of the high frequency alleles are used to calculate the percent fetal cell-free DNA in the sample, e.g., sums of low frequency alleles can be divided by sums of high and low frequency alleles.

FIG. 1 is a simplified flow chart of the general steps utilized in determination of percent fetal contribution of cell-free DNA in a maternal sample from an egg donor pregnancy. FIG. 1 shows method 100, where in a first step 101a maternal sample is provided from a pregnant woman with an egg donor pregnancy comprising maternal and fetal cell-free DNA. The maternal sample may be in the form of whole blood, plasma, or serum. Optionally, he cell-free DNA is isolated from the sample prior to further analysis. At step 103, two or more polymorphic nucleic acid regions are interrogated in the sell-free DNA from the sample. Interrogation may comprise sequencing of selected polymorphic nucleic acids followed by selective amplification of those nucleic acid regions, increasing the copy number of the selected nucleic acid regions in a manner that allows preservation of the relative quantity of the selected nucleic acid regions in the initial sample. Optionally, the nucleic acid regions may then be universally amplified, e.g., through the use of universal primer sequences. Universal amplification may be performed prior to or during a determination step. At step 105, the interrogated nucleic acid regions are detected. Detection may comprise detection methods such as sequence determination or hybridization. Detection of selected nucleic acid sequences may be carried out through detection of one or more indices associated with the selected polymorphic region, e.g. locus indices or allele indices. At step 107, a relative frequency of polymorphisms in the interrogated nucleic acid regions are determined to identify egg donor informative loci. In step 109, percent fetal cell-free DNA is calculated using the identified egg donor informative loci. Calculation of percent fetal may comprise dividing the sum of the low frequency alleles by the sum of the combined low and high frequency alleles. These concepts will be discussed in further detail below.

Egg donor pregnancies differ from traditional pregnancies in determination of percent fetal contribution in a maternal sample, given that the carrier mother and the fetus does not share approximately half of the genetic information of the mother. In a maternal sample wherein the fetus is the genetic offspring of the mother, the maternal DNA and the fetal DNA generally have at least one allele in common at any particular locus, although certain alleles may differ due to, e.g., mutations. However, in an egg donor pregnancy, the maternal DNA and the fetal DNA may not have any alleles in common at a particular locus. For example, both the maternal genome and the fetal genome may comprise homozygous alleles at the same locus, but both maternal alleles may be different from the fetal alleles.

Egg donor informative loci for use in the resent invention are loci in which at least one fetal allele is different from the maternal alleles. For example, the maternal genome may comprise homozygous alleles at a particular locus while the fetal genome comprises heterozygous alleles, wherein the maternal and fetal genomes have one allele in common. Alternatively, the maternal genome may comprise heterozygous alleles at a particular locus and the fetal genome may comprise homozygous alleles, wherein the maternal and fetal DNA have one allele in common. In yet another example, as described above, the maternal genome may comprise homozygous alleles at a particular locus and the fetal genome may comprise homozygous alleles at a particular locus, wherein both maternal alleles are different from the fetal alleles.

FIG. 2 is a table illustrating the 14 possible combinations of maternal genotype, egg donor genotype and fetal genotype in an egg donor pregnancy at a particular locus, and further shows their classifications as informative versus non-formative loci. In FIG. 2, A is used to represent a first type of allele while B is used to represent a different type of allele. In Combination 201, for example, the maternal genotype is AA, the egg donor genotype is AA and the fetal genotype is AA. In this situation, the locus is not informative for purposes of evaluation of percent fetal contribution since the fetal DNA does not comprise at least one allele that is different form the maternal DNA. In another example, Combination 204 comprises a maternal genotype of AA, and egg donor genotype of AB, and a fetal genotype of AB. This is an egg donor informative locus because the fetal DNA has at least one allele that is different from the maternal alleles at that locus. In yet another example, Combination 105 comprises a maternal genotype AA, egg donor genotype AB and fetal genotype BB. This is an egg donor informative locus because the fetal source has at least one allele that is different from an allele of the maternal source, and in fact both of the alleles of the fetal DNA are different from the maternal DNA at that locus.

In some specific aspects, the relative fetal contribution of maternal DNA at an allele of interest can be compared to the non-maternal contribution at that allele to determine approximate fetal DNA concentration in the sample.

Determination of Fetal DNA Content in a Maternal Sample Using Fetal Autosomal Polymorphisms and Genetic Variations As described above, in a maternal sample from an egg donor pregnancy, the DNA from a fetus may not have any alleles in common with the carrier mother at a particular locus. Determining the loci in which the fetus has at least one allele that is different from the alleles of the carrier mother can allow the estimation of percent fetal DNA in a maternal sample, and thus provide information used to calculate the statistically significant differences in chromosomal frequencies for chromosomes of interest.

In certain aspects, the determination of fetal polymorphisms requires targeted SNP and/or mutation analysis to identify the presence of fetal DNA in a maternal sample. In some aspects, the use of prior genotyping of the father and mother can be performed. For example, the parents may have undergone such genotype determination for identification of disease markers, e.g., determination of the genotype for disorders such as cystic fibrosis, muscular dystrophy, spinal muscular atrophy or even the status of the RhD gene may be determined. Such difference in polymorphisms, copy number variants or mutations can be used to determine the percentage fetal contribution in a maternal sample.

In one preferred aspect, the percent fetal cell-free DNA in a maternal sample can be quantified using multiplexed SNP detection without using prior knowledge of the maternal or paternal genotype. In this aspect, two or more selected polymorphic nucleic acid regions with a known SNP in each region are used. In a preferred aspect, the selected polymorphic nucleic acid regions are located on an autosomal chromosome that is unlikely to be aneuploidy, e.g., Chromosomes 1-12. The selected polymorphic nucleic acid regions from the maternal are amplified. In a preferred aspect, the amplification is universal.

In a preferred embodiment, the selected polymorphic nucleic acid regions are amplified in one reaction in one vessel. Each allele of the selected polymorphic nucleic acid regions in the maternal sample is then determined and quantified. In a preferred aspect, high throughput sequencing is used for such determination and quantification. Following sequence determination, loci are identified where the maternal and fetal genotypes are different, e.g., the maternal genotype is homozygous and the fetal genotype is heterozygous, or both the maternal and fetal genotypes are homozygous and both fetal alleles are different from the maternal alleles. This identification can be done by observing a high relative frequency of one allele (>60%) and a low relative frequency (<20% and >0.15%) of the other allele for a particular selected nucleic acid region. The use of multiple loci is particularly advantageous as it reduces the amount of variation in the measurement of the abundance of the alleles. All or a subset of the loci that meet this requirement are used to determine fetal concentration through statistical analysis.

Fetal concentration in an egg donor pregnancy is determined by accounting for egg donor informative loci in which both fetal alleles are different from the maternal alleles. Detection of extra polymorphic nucleic acids may result in overestimation of the percent fetal contribution such loci are not accounted for either before or after a determination step. In specific aspects, only the fetal alleles that both differ from the alleles of the mother are used in the determination. In other aspects, the fetal alleles that both differ from the maternal alleles are excluded before or after determination. In more specific aspects, fetal alleles in which only one allele is different from the maternal alleles as well as alleles. In one aspect, fetal concentration is estimated by determining a relative frequency of low frequency alleles from two or more loci, determining a relative frequency of high frequency alleles, and comparing the relative frequency of low frequency alleles to the frequency of both low and high frequency alleles.

In one aspect, percent fetal contribution is determined by analysis of a subset of loci, such as a subset wherein either the maternal or fetal genotype is homozygous, and the other genotype is heterozygous. In a specific aspect, fetal concentration is determined using the frequency of low frequency alleles from two or more selected loci and the frequency of high and low frequency alleles. In one aspect, fetal concentration is determined by summing the low frequency alleles from two or more loci together and dividing by the sum of the high and low frequency alleles. In another aspect, the percent fetal cell-free DNA is determined by averaging the low frequency alleles from two or more loci, dividing by the average of the high and low frequency alleles and multiplying by two. Isolation of the subset of loci may be done prior to determination of the relative frequency of alleles or after determination of the relative frequency of alleles.

In another aspect, percent fetal contribution is determined by analyzing a subset of loci wherein both the maternal and fetal genotype are homozygous and both fetal alleles are different from the maternal alleles. In a specific aspect, fetal concentration is determined using the frequency of low frequency alleles from two or more selected loci and the frequency of high and low frequency alleles. In certain specific aspects, the percent fetal cell-free DNA is determined by summing the low frequency alleles from two or more loci and dividing by the sum of the high and low frequency alleles. In another aspect, the percent fetal contribution is determined by averaging the low frequency alleles from two or more loci and dividing by the average of the high and low frequency alleles. Isolation of a subset of loci may be done prior to determination of the relative frequency of alleles or after determination of the relative frequency of alleles.

In yet another aspect, percent fetal contribution is determined by analysis of all egg donor informative loci comprising polymorphic nucleic acids. For example, all loci are used in which either the maternal or fetal genotype is homozygous and the other is heterozygous and all loci in which both the maternal and fetal genotypes are homozygous and both fetal alleles are different from the maternal alleles. In one aspect, percent fetal contribution is determined using a combination of calculations: for the loci in which both the maternal and fetal genotypes are homozygous and both fetal alleles are different from the maternal alleles, by using the frequency of low frequency alleles from two or more selected loci and the frequency of high and low frequency alleles and, for the loci in which either the maternal or fetal genotype is homozygous and the other is heterozygous, by using the frequency of low frequency alleles from two or more loci together and the frequency of the high and low frequency alleles.

For many alleles, maternal and fetal sequences may be homozygous and identical, and as this information is not distinguishing between maternal and fetal DNA it is not useful in the determination of percent fetal DNA in a maternal sample. The present invention utilizes allelic information where there is a distinguishable difference between the fetal and maternal DNA (e.g., a fetal allele containing at least one allele that differs from the maternal allele) in calculations of percent fetal. Data pertaining to allelic regions that are the same for the maternal and fetal DNA are thus not selected for analysis, or are removed from the pertinent data prior to determination of percentage fetal DNA so as not to swamp out the useful data.

Exemplary methods for quantifying fetal DNA in maternal plasma can be found, e.g., in Chu et al., *Prenat Diagn* 2010; 30:1226-1229, which is incorporated herein by reference.

In one aspect, selected nucleic acid regions may be excluded if the amount or frequency of the region appears to be an outlier due to experimental error, or from idiopathic genetic bias within a particular sample. In another aspect, selected nucleic acids may undergo statistical or mathematical adjustment such as normalization, standardization, clustering, or transformation prior to determination of the frequency of low and high frequency alleles. In another aspect, selected nucleic acids may undergo both normalization and data experimental error exclusion prior to determination of the frequency of low and high frequency alleles.

In a preferred aspect, 12 or more loci are used for the analysis. In another preferred aspect, 24 or more loci are used for the analysis. In another preferred aspect, 48 or more loci are used for the analysis. In another aspect, one or more indices are used to identify the sample, the locus, the allele or the identification of the nucleic acid.

In one preferred aspect, the percentage fetal contribution in a maternal sample can be quantified using tandem SNP detection in the maternal and fetal alleles. Techniques for identifying tandem SNPs in DNA extracted from a maternal sample are disclosed in Mitchell et al, U.S. Pat. No. 7,799,531 and U.S. patent application Ser. Nos. 12/581,070, 12/581,083, 12/689,924, and 12/850,588. These describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample, as described in the Mitchell et al. disclosures, and used to determine the percent fetal contribution in the maternal sample.

Detecting Chromosomal Aneuploidies

In certain aspects, methods of the invention provide mechanisms for identifying fetal chromosomal aneuploidies in maternal samples from an egg donor pregnancy comprising both maternal and fetal DNA. In certain aspects, identification of fetal aneuploidy may be carried out by any suitable method, as will be apparent to one skilled in the art upon reading the present specification. The methods include polymorphic detection, such as SNP detection of specific nucleic acids, or preferably non-polymorphic detection based on fetal and maternal sequences, and preferably conserved non-polymorphic sequences between the mother and fetus. Exemplary methods are as follows:

In some aspects, nucleic acids can be selected from a maternal sample prior to detection, i.e. selectively isolated from a maternal sample prior to detection using amplification or capture techniques such as hybridization. In another specific aspect, the nucleic acids used in fetal aneuploidy detection in an egg donor pregnancy may be selected after detection, e.g., by filtering frequency data generated from techniques such as massively parallel shotgun sequencing of nucleic acids within the maternal sample.

In some specific aspects, fetal aneuploidy detection in an egg donor pregnancy employs selective sequencing methods that interrogate chromosome-specific loci, enabling highly multiplexed sequencing of selected loci from specific chromosomes of interest. Chromosome-selective sequencing can be used to assay simultaneously polymorphic and non-polymorphic loci in a single reaction, enabling determination of both fetal aneuploidy and percent contribution of fetal nucleic acids in the maternal sample. Subsequently, a novel risk calculation of the invention can employed, which leverages fetal aneuploidy and fetal contribution estimates to compute the likelihood of fetal aneuploidies (e.g., fetal trisomy) in each subject.

In one aspect, the present invention utilizes analysis of random DNA segments, such as, that described in, e.g., Quake et al., U.S. Pat. Nos. 8,008,018, 7,888,017, and Shoemaker et al., to determine fetal aneuploidy. Briefly, the quantity of nucleic acids within a mixed sample such as a maternal sample can be differentially detected using selected nucleic acid sequences. The nucleic acids may be genomic DNA or RNA, and preferably are mRNA. In the case of mRNA, one may choose target sequences corresponding to genes that are highly expressed in the fetus. The nucleic acids in each sample are detected with one or more sequence-specific probes directed to at least one of two target sequences in the nucleic acids to obtain a detectible reaction product. A probe specific to an interrogated chromosome is combined with the reaction sample, along with a control probe specific to another (e.g., non-interrogated) chromosome. In most cases, the reaction products will be from maternal nucleic acids, but a small number of reaction products will be from fetal nucleic acids. In order to distinguish random variation from fetal results, a large number of reactions are run, and statistical processes are applied to the results. Labeling and detection in the present process is used to distinguish the presence or absence of a single target sequence, referred to as "digital analysis," although it may be performed with sensitive nucleic acid detection processes which distinguish between one and more than one target sequence in a discrete sample.

In another example, massively parallel sequencing of nucleic acids (e.g., DNA fragments randomly selected from the sample) is used to determine the sequence of the nucleic acids in the maternal sample to determine selected frequency of the nucleic acids within the maternal sample. Exemplary techniques for performing massively parallel sequencing of nucleic acid sequences include those disclosed in U.S. Pat. Nos. 8,318,430, 8,296,076 and 8,195,415, and in U.S. applications US20090029377, 20090087847, 20100112590, 20110312503, 20110319272, 20110246083, 20110318734, 20120003635, 20120003636, 20120003637, 20120190559, and 20120208708. For detection of a chromosome frequency abnormality (e.g., a trisomy), the sequenced nucleic acids are identified as being from a first chromosome, and the total amounts of nucleic acids from at least one first chromosome in the maternal sample are compared to total amounts of nucleic acids from at least one second chromosome in the maternal sample. The total nucleic acid amounts include the nucleic acids from both the fetus and mother in the maternal sample, and the nucleic acids from the fetus are not differentiated from the maternal in determining the frequency of the nucleic acids corresponding to the chromosome frequency. Where one first chromosome is presumed to be euploid, and the second chromosome is suspected to be aneuploid, the total numbers of nucleic acids for the first and second chromosomes are compared to determine the presence or absence of said aneuploidy.

In more specific aspects, the samples used for massively parallel sequencing of nucleic acids are enriched for polymorphic regions. Exemplary techniques for performing enrichment include those disclosed in, e.g., WO2011091063, WO2011091046 and US Pat Appln No. 20110230358. Briefly, a portion of a maternal sample comprising cell free DNA is amplified to augment the number of copies of the one or more polymorphic sequences in the sample, and the amplified portions of nucleic acids are then added back to the original sample for sequencing. Alternatively, the sample is subjected to whole genome sequencing to obtain a plurality of sequence tags, and the sequences of the tags are compared to the sequence of multiple reference polymorphisms.

In some aspects, the nucleic acids are sequenced using array-based hybridization processes, such as those described in U.S. Pat. Pub. No. 2011/0172111. In other aspects, the biomolecules are detected using nanopore technology detection, such as those described in U.S. Pat. Pub. No. 2011/0124518.

In another aspect, the nucleic acids are sequenced and compared using polymorphisms that differentiate between maternal and fetal alleles in a sample, using methods such as those described in U.S. Pat. Nos. 7,727,720, 7,718,370, 7,598,060, 7,442,506, 7,332,277, 7,208, 274, and 6,977,162. Briefly, the methods utilize polymorphic detection to identify chromosomal abnormalities. Sequences are determined at alleles that are homozygous in the mother and heterozygous in the fetus, and a ratio for the heterozygous alleles are determined. The ratio for the heterozygous alleles is used to indicate the presence or absence of a chromosomal abnormality.

In yet another aspect, determination of fetal aneuploidies utilizes identification of tandem polymorphisms, such as that described in, e.g., U.S. Pat. No. 7,799,531, and U.S. Pub. Nos. 2011/0117548, 2011/0059451, 2010/0184044, 2010/184043, and 2008/0020390. Briefly, tandem SNPs are detected and used to differentiate maternal and fetal alleles in a maternal sample to detect fetal chromosomal abnormalities through comparison of maternal DNA to fetal DNA.

In a preferred aspect, the determination of fetal aneuploidy utilizes selected amplification of representative loci. Such techniques are disclosed in, e.g., U.S. application Ser. Nos. 13/013,732, 13/205,490, 13/205,570, and 13/205,603, all of which are incorporated herein in their entirety. These techniques utilize detection of genomic regions using fixed sequence oligonucleotides and joining the fixed sequence oligonucleotides via ligation and/or extension. This can be accomplished using a combination of ligation and amplification, e.g., the ligation of two or more fixed sequence oligonucleotides and optionally a bridging oligonucleotide that is complementary to a region between the fixed sequence oligonucleotides. In another example, this can be accomplished using a combination of extension, ligation and amplification.

In some aspects, variations for the normal population are determined from normal samples that have a similar proportion of fetal DNA. For example, an expected chromosomal dosage for trisomy in a DNA sample with a specific percent fetal cell free DNA can be calculated by adding the percent contribution from the aneuploid chromosome. The chromosomal dosage for the sample may then be compared to the chromosomal dosage for a normal fetus and to an expected chromosomal dosage if triploid to determine statistically, using the variation of the chromosomal dosage, if the sample is more likely normal or triploid, and the statistical probability that it is one or the other.

In a preferred aspect, the nucleic acid regions selected for analysis in the maternal sample include in a single reaction both nucleic acid regions for determination of percent fetal contribution as well as nucleic acid regions corresponding to two or more chromosomes used to detect a chromosomal dosage abnormality. The use of a single reaction helps to minimize the risk of contamination or bias that may be introduced using separate reactions, which may otherwise skew results. In fact, the methods of the present invention are preferably performed as multiplexed or even highly-multiplexed reactions, where both polymorphic and non-polymorphic loci (for determining percent fetal contribution and fetal aneuploidy, respectively) are interrogated in a single reaction for each sample. In preferred embodiments, the multiplexing assays described in U.S. application Ser. Nos. 13/013,732, 13/205,490, 13/205,570, and 13/205,603 are used, as these assays query both polymorphic and non-polymorphic loci in a maternal sample in a single multiplexed reaction.

In other aspects, one or more selected nucleic acid regions may be interrogated both for determination of fetal nucleic acid proportion as well as detection of fetal chromosomal abnormalities. Utilizing the same regions for both fetal percent contribution and detection of fetal aneuploidies further aids in minimizing bias due to experimental error or contamination.

Amplification Methods

Numerous amplification methods can be used to provide the amplified nucleic acids that are analyzed in the assay systems of the invention, and such methods are preferably used to increase the copy numbers of a nucleic acid region of interest in a maternal sample from an egg donor pregnancy in a manner that allows preservation of information concerning the initial content of the nucleic acid region in the maternal sample. Although not all combinations of amplification and analysis are described herein in detail, it is well within the skill of those in the art to utilize different amplification methods and/or analytic tools to isolate and/or analyze the nucleic acids of region consistent with this specification, and such variations will be apparent to one skilled in the art upon reading the present disclosure.

Such amplification methods include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. Other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In some aspects DNA is amplified by multiplex locus-specific PCR. In a preferred aspect the DNA is amplified using adaptor-ligation and single primer PCR. Other available methods of amplification include balanced PCR (Makrigiorgos, et al.

(2002), Nat Biotechnol, Vol. 20, pp. 936-9) and self-sustained sequence replication (Guatelli et al., Proc. Natl. Acad. Sci. USA 87: 1874, 1990). Based on such methodologies, a person skilled in the art can readily design primers in any suitable regions 5' and 3' to a nucleic acid region of interest. Such primers may be used to amplify DNA of any length so long that it contains the nucleic acid region of interest in its sequence.

The length of an amplified selected nucleic acid from a genomic region of interest is generally long enough to provide enough sequence information to distinguish it from other nucleic acids that are amplified and/or selected. Generally, an amplified nucleic acid is at least about 16 nucleotides in length, and more typically, an amplified nucleic acid is at least about 20 nucleotides in length. In a preferred aspect of the invention, an amplified nucleic acid is at least about 30 nucleotides in length. In a more preferred aspect of the invention, an amplified nucleic acid is at least about 32, 40, 45, 50, or 60 nucleotides in length. In other aspects of the invention, an amplified nucleic acid can be about 100, 150 or up to 200 in length.

In certain aspects, the selective amplification uses one or a few rounds of amplification with primer pairs comprising nucleic acids complementary to the selected nucleic acids. In other aspects, the selective amplification comprises an initial linear amplification step. These methods can be particularly useful if the starting amount of DNA is quite limited, e.g., where the cell-free DNA in a sample is available in limited quantities. This mechanism increases the amount of DNA molecules that are representative of the original DNA content, and help to reduce sampling error where accurate quantification of the DNA or a fraction of the DNA (e.g., fetal DNA contribution in a maternal sample) is needed.

Thus, in one aspect, a limited number of cycles of sequence-specific amplification are performed on the starting maternal sample comprising cell-free DNA. The number of cycles is generally less than that used for a typical PCR amplification, e.g., 5-30 cycles or fewer. Primers or probes may be designed to amplify specific genomic segments or regions. The primers or probes may be modified with an end label at the 5' end (e.g., with biotin) or elsewhere along the primer or probe such that the amplification products could be purified or attached to a solid substrate (e.g., bead or array) for further isolation or analysis. In a preferred aspect, the primers are multiplexed such that a single reaction yields multiple DNA fragments from different regions. Amplification products from the linear amplification could then be further amplified with standard PCR methods or with additional linear amplification.

For example, cell-free DNA can be isolated from blood, plasma, or serum from a pregnant woman, and incubated with primers against a set number of nucleic acid regions that correspond to chromosomes of interest. Preferably, the number of primer pairs used for initial amplification will be 12 or more, more preferably 24 or more, more preferably 36 or more, even more preferably 48 or more, and even more preferably 96 or more. Each of the primers corresponds to a single nucleic acid region, and is optionally tagged for identification and/or isolation. A limited number of cycles, preferably 10 or fewer, are performed. The amplification products are subsequently isolated, e.g., when the primers are linked to a biotin molecule the amplification products can be isolated via binding to avidin or streptavidin on a solid substrate. The products are then subjected to further biochemical processes such as further amplification with other primers (e.g., universal primers) and/or detection techniques such as sequence determination and hybridization.

Efficiencies of amplification may vary between sites and between cycles so that in certain systems normalization may be used to ensure that the products from the amplification are representative of the nucleic acid content starting material. One practicing the assay system of the invention can utilize information from various samples to determine variation in nucleic acid levels, including variation in different nucleic acid regions in individual samples and/or between the same nucleic acid regions in different samples following the limited initial linear amplification. Such information can be used in normalization to prevent skewing of initial levels of DNA content.

Universal Amplification

In preferred aspects of the invention, the selectively amplified nucleic acid regions are preferably amplified following selective amplification or enrichment, either prior to or during the nucleic acid region detection techniques. In another aspect of the invention, nucleic acid regions are selectively amplified during the nucleic acid region detection technique without any prior amplification. In a multiplexed assay system, this is preferably done through use of universal amplification of the various nucleic acid regions to be analyzed using the assay systems of the invention. Universal primer sequences are added to the selectively amplified nucleic acid regions, either during or following selective amplification, so that they may be further amplified in a single universal amplification reaction. For example, these universal primer sequences may be added to the nucleic acids regions during the selective amplification process, i.e., the primers for selective amplification have universal primer sequences that flank a locus. Alternatively, adapters comprising universal amplification sequences can be added to the ends of the selected nucleic acids as adapters following amplification and isolation of the selected nucleic acids from the maternal sample.

In one exemplary aspect, nucleic acids are initially amplified from a maternal sample using primers comprising a region complementary to selected regions of the chromosomes of interest and universal priming sites. The initial selective amplification is followed by a universal amplification step to increase the number of nucleic acid regions for analysis. This introduction of primer regions to the initial amplification products allows a subsequent controlled universal amplification of all or a portion of selected nucleic acids prior to or during analysis, e.g., sequence determination.

Bias and variability can be introduced during DNA amplification, such as that seen during polymerase chain reaction (PCR). In cases where an amplification reaction is multiplexed, there is the potential that loci will amplify at different rates or efficiency. Part of this may be due to the variety of primers in a multiplex reaction with some having better efficiency (i.e. hybridization) than others, or some working better in specific experimental conditions due to the base composition. Each set of primers for a given locus may behave differently based on sequence context of the primer and template DNA, buffer conditions, and other conditions. A universal DNA amplification for a multiplexed assay system will generally introduce less bias and variability.

Accordingly, in a preferred aspect, a small number (e.g., 1-10, preferably 3-5) of cycles of selective amplification or nucleic acid enrichment in a multiplexed mixture reaction are performed, followed by universal amplification using introduced universal priming sites. The number of cycles using universal primers will vary, but will preferably be at least 10 cycles, more preferably at least 5 cycles, even more preferably 20 cycles or more. By moving to universal amplification following one or a few selective amplification cycles, the bias of having certain loci amplify at greater rates than others is reduced.

Optionally, the assay system will include a step between the selective amplification and universal amplification to remove any excess nucleic acids that are not specifically amplified in the selective amplification.

The whole product or an aliquot of the product from the selective amplification may be used for the universal amplification. The same or different conditions (e.g., polymerase, buffers, and the like) may be used in the amplification steps, e.g., to ensure that bias and variability is not inadvertently introduced due to experimental conditions. In addition, variations in primer concentrations may be used to effectively limit the number of sequence specific amplification cycles.

In certain aspects, the universal primer regions of the primers or adapters used in the assay system are designed to be compatible with conventional multiplexed assay methods that utilize general priming mechanisms to analyze large numbers of nucleic acids simultaneously in one reaction in one vessel. Such "universal" priming methods allow for efficient, high volume analysis of the quantity of nucleic acid regions present in a maternal sample from an egg donor pregnancy, and allow for comprehensive quantification of the presence of nucleic acid regions within such a maternal sample for the determination of aneuploidy.

Examples of such assay methods include, but are not limited to, multiplexing methods used to amplify and/or genotype a variety of samples simultaneously, such as those described in Oliphant et al., U.S. Pat. No. 7,582,420, which is incorporated herein by reference.

Some aspects utilize coupled reactions for multiplex detection of nucleic acid sequences where oligonucleotides from an early phase of each process contain sequences which may be used by oligonucleotides from a later phase of the process. Exemplary processes for amplifying and/or detecting nucleic acids in samples can be used, alone or in combination, including but not limited to the methods described below, each of which are incorporated by reference in their entirety for purposes of teaching various elements that can be used in the assay systems of the invention.

In certain aspects, the assay system of the invention utilizes one of the following combined selective and universal amplification techniques: (1) LDR coupled to PCR; (2) primary PCR coupled to secondary PCR coupled to LDR; and (3) primary PCR coupled to secondary PCR. Each of these aspects of the invention has particular applicability in detecting certain nucleic acid characteristics. However, each requires the use of coupled reactions for multiplex detection of nucleic acid sequence differences where oligonucleotides from an early phase of each process contain sequences which may be used by oligonucleotides from a later phase of the process.

Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe the use of the ligase detection reaction with detection reaction ("LDR") coupled with polymerase chain reaction ("PCR") for nucleic acid detection.

Barany et al., U.S. Pat. Nos. 7,556,924 and 6,858,412, describe the use of padlock probes (also called "precircle probes" or "multi-inversion probes") with coupled ligase detection reaction ("LDR") and polymerase chain reaction ("PCR") for nucleic acid detection.

Barany et al., U.S. Pat. Nos. 7,807,431, 7,709,201, and 7,198, 814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping.

Ronaghi et al., U.S. Pat. No. 7,622,281 describes amplification techniques for labeling and amplifying a nucleic acid using an adapter comprising a unique primer and a barcode.

In addition to the various amplification techniques, numerous methods of sequence determination are compatible with the assay systems of the inventions. Preferably, such methods include "next generation" methods of sequencing. Exemplary methods for sequence determination include, but are not limited to, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459, 311 and 6,210,891; Balasubramanian, U.S. Pat. Nos. 7,232, 656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891, and ligation-based sequencing determination methods, e.g., Drmanac et al., U.S. Pat. Appln No. 20100105052, and Church et al, U.S. Pat. Appln Nos. 20070207482 and 20090018024.

Alternatively, nucleic acid regions of interest can be selected and/or identified using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386, 749, 6,391,623.

The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964).

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Patent application 60/364,731 and in PCT Application PCT/US99/06097 (published as WO99/47964).

Use of Indices in the Assay Systems of the Invention

In certain aspects, all or a portion of the nucleic acids of interest are directly detected using the described techniques, e.g., sequence determination or hybridization. In certain aspects, however, the nucleic acids of interest are associated with one or more indices that are identifying for a selected nucleic acid region or a particular sample being analyzed. The detection of the one or more indices can serve as a surrogate detection mechanism of the selected nucleic acid region, or as confirmation of the presence of a particular selected nucleic acid region if both the sequence of the index and the sequence of the nucleic acid region itself are determined. These indices are preferably associated with the selected nucleic acids during an amplification step using primers that comprise both the index and sequence regions that specifically hybridize to the nucleic acid region.

In one example, the primers used for selective amplification of a nucleic acid region are designed to provide a locus index between the region complementary to a locus of interest and a universal amplification priming site. The locus index is unique for each selected nucleic acid region and representative of a locus on a chromosome of interest or reference chromosome, so that quantification of the locus index in a sample provides quantification data for the locus and the particular chromosome containing the locus.

In another example, the primers used for amplification of a selected nucleic acid region are designed to provide an allele index between the region complementary to a locus of interest and a universal amplification priming site. The allele index is unique for particular alleles of a selected nucleic acid region and representative of a locus variation present on a chromosome of interest or reference chromosome, so that quantification of the allele index in a sample provides quantification data for the allele and the relative frequencies of the allelic indices for a particular locus provides quantification data for both the locus and the particular chromosome containing the locus.

In another aspect, the primers used for amplification of the selected nucleic acid regions to be analyzed for a maternal sample from an egg donor pregnancy are designed to provide an identification index between the region complementary to a locus of interest and a universal amplification priming site. In such an aspect, a sufficient number of identification indices are present to uniquely identify each selected nucleic acid region in the sample. Each nucleic acid region to be analyzed is associated with a unique identification index, so that the identification index is uniquely associated with the selected nucleic acid region. Quantification of the identification index in a sample provides quantification data for the associated selected nucleic acid region and the chromosome corresponding to the selected nucleic acid region. The identification locus may also be used to detect any amplification bias that occurs downstream of the initial isolation of the selected nucleic acid regions from a sample.

In certain aspects, only the locus index and/or the identification index (if present) are detected and used to quantify the selected nucleic acid regions in a sample. In another aspect, a count of the number of times each locus index occurs with a unique identification index is done to determine the relative frequency of a selected nucleic acid region in a sample.

In some aspects, indices representative of the sample from which a nucleic acid is isolated are used to identify the source of the nucleic acid in a multiplexed assay system. In such aspects, the nucleic acids are uniquely identified with the sample index. Those uniquely identified oligonucleotides may then be combined into a single reaction vessel with nucleic acids from other samples prior to sequencing. The sequencing data is first segregated by each unique sample index prior to determining the frequency of each target locus for each sample and prior to determining whether there is a chromosomal abnormality for each sample. For detection, the sample indices, the locus indices, and the identification indices (if present) are sequenced.

In aspects of the invention using indices, the selective amplification primers are preferably designed so that indices comprising identifying information are coded at one or both ends of the primer. Alternatively, the indices and universal amplification sequences can be added to the selectively amplified nucleic acids following initial selective amplification.

The indices are non-complementary but unique sequences used within the primer to provide information relevant to the selective nucleic acid region that is isolated and/or amplified using the primer. The advantage of this is that information on the presence and quantity of the selected nucleic acid region can be obtained without the need to determine the actual sequence itself, although in certain aspects it may be desirable to do so. Generally, however, the ability to identify and quantify a selected nucleic acid region through identification of one or more indices will decrease the length of sequencing required as the loci information is captured at the 3' or 5' end of the isolated selected nucleic acid region. Use of indices identification as a surrogate for identification of selected nucleic acid regions may also reduce error since longer sequencing reads are more prone to the introduction or error.

In addition to locus indices, allele indices and identification indices, additional indices can be introduced to primers to assist in the multiplexing of samples. For example, correction indices which identify experimental error (e.g., errors introduced during amplification or sequence determination) can be used to identify potential discrepancies in experimental procedures and/or detection methods in the assay systems. The order and placement of these indices, as well as the length of these indices, can vary, and they can be used in various combinations.

The primers used for identification and quantification of a selected nucleic acid region may be associated with regions complementary to the 5' of the selected nucleic acid region, or in certain amplification regimes the indices may be present on one or both of a set of amplification primers which comprise sequences complementary to the sequences of the selected nucleic acid region. The primers can be used to multiplex the analysis of multiple selected nucleic acid regions to be analyzed within a sample, and can be used either in solution or on a solid substrate, e.g., on a microarray or on a bead. These primers may be used for linear replication or amplification, or they may create circular constructs for further analysis.

Variation Minimization within and Between Samples

One challenge with the detection of chromosomal abnormalities in a maternal sample from an egg donor pregnancy is that often the DNA from the cell type with the putative chromosomal abnormality is present in much lower abundance than the DNA from normal cell type. In the case of a mixed maternal sample containing fetal and maternal cell-free DNA, the cell free fetal DNA as a percentage of the total cell-free DNA may vary from less than one to forty percent, and most commonly is present at or below twenty percent and frequently at or below ten percent. In the detection of an aneuploidy such as Trisomy 21 (Down Syndrome) in the fetal DNA of such mixed maternal sample, the relative increase in Chromosome 21 is 50% in the fetal DNA and thus as a percentage of the total DNA in a maternal sample where, as an example, the fetal DNA is 5% of the total, the increase in Chromosome 21 as a percentage of the total is 2.5%. If one is to detect this difference robustly through the methods described herein, the variation in the measurement of Chromosome 21 has to be much less than the percent increase of Chromosome 21.

The variation between levels found between samples and/or for nucleic acid regions within a sample may be minimized in a combination of analytical methods, many of which are described in this application. For instance, variation is lessened by using an internal reference in the assay. An example of an internal reference is the use of a chromosome present in a "normal" abundance (e.g., disomy for an autosome) to compare against a chromosome present in putatively abnormal abundance, such as aneuploidy, in the same sample. While the use of one such "normal" chromosome as a reference chromosome may be sufficient, it is also possible to use many normal chromosomes as the internal reference chromosomes to increase the statistical power of the quantification.

One method of using an internal reference is to calculate a ratio of abundance of the putatively abnormal chromosomes to the abundance of the normal chromosomes in a sample, called a chromosomal ratio. In calculating the chromosomal ratio, the abundance or counts of each of the nucleic acid regions for each chromosome are quantified to calculate the total counts for each chromosome. The total counts for one chromosome are then divided by the total counts for a different chromosome to create a chromosomal ratio for those two chromosomes.

Alternatively, a chromosomal ratio for each chromosome may be calculated by first quantifying the relative frequency (e.g. summing) of each of the nucleic acid regions for each chromosome, and then comparing the relative frequencies of one chromosome to the relative frequency of two or more chromosomes (e.g. dividing the sum for one chromosome by the total sum for two or more chromosomes). Once calculated, the chromosomal ratio is then compared to the average chromosomal ratio from a normal population.

The average may be the mean, median, mode or other average, with or without normalization and exclusion of outlier data. In a preferred aspect, the mean is used. In developing the data set for the chromosomal ratio from the normal population, the normal variation of the measured chromosomes is calculated. This variation may be expressed a number of ways, most typically as the coefficient of variation, or CV. When the chromosomal ratio from the sample is compared to the average chromosomal ratio from a normal population, if the chromosomal ratio for the sample falls statistically outside of the average chromosomal ratio for the normal population, the sample contains an aneuploidy. The criteria for setting the statistical threshold to declare an aneuploidy depend upon the variation in the measurement of the chromosomal ratio and the acceptable false positive and false negative rates for the desired assay. In general, this threshold may be a multiple of the variation observed in the chromosomal ratio. In one example, this threshold is three or more times the variation of the chromosomal ratio. In another example, it is four or more times the variation of the chromosomal ratio. In another example it is five or more times the variation of the chromosomal ratio. In another example it is six or more times the variation of the chromosomal ratio. In the example above, the chromosomal ratio is estimated by determining the relative frequencies (e.g. by summing the counts) of nucleic acid regions by chromosome. Typically, the same number of nucleic acid regions for each chromosome is used. An alternative method for generating the chromosomal ratio would be to calculate the average relative frequency for the nucleic acid regions for each chromosome. The average may be any estimate of the mean, median or mode, although typically an average is used. The average may be the mean of all relative frequencies or some variation such as a trimmed or weighted average. Once the average relative frequencies for each chromosome have been calculated, the average relative frequencies for each chromosome may be compared to other chromosomes to obtain a chromosomal ratio between two chromosomes, the average relative frequencies for each chromosome may be compared to the relative frequencies for all measured chromosomes to obtain a chromosomal ratio for each chromosome as described above. As highlighted above, the ability to detect an aneuploidy in a maternal sample from an egg donor pregnancy where the putative DNA is in low relative abundance depends greatly on the variation in the measurements of different nucleic acid regions in the assay. Numerous analytical methods can be used which reduce this variation and thus improve the sensitivity of this method to detect aneuploidy.

One method for reducing variability of the assay is to increase the number of nucleic acid regions used to calculate the abundance of the chromosomes. In general, if the measured variation of a single nucleic acid region of a chromosome is X % and Y different nucleic acid regions are measured on the same chromosome, the variation of the measurement of the chromosomal abundance calculated by summing or averaging the abundance of each nucleic acid region on that chromosome will be approximately X % divided by $Y^{1/2}$. Stated differently, the variation of the measurement of the chromosome abundance would be approximately the average variation of the measurement of each nucleic acid region's abundance divided by the square root of the number of nucleic acid regions.

In a preferred aspect of this invention, the number of nucleic acid regions measured for each chromosome is at least 24. In another preferred aspect of this invention, the number of nucleic acid regions measured for each chromosome is at least 48. In another preferred aspect of this invention, the number of nucleic acid regions measured for each chromosome is at least 100. In another preferred aspect of this invention the number of nucleic acid regions measured for each chromosome is at least 200. There is incremental cost to measuring each nucleic acid region and thus it is important to minimize the number of each nucleic acid region. In a preferred aspect of this invention, the number of nucleic acid regions measured for each chromosome is less than 2000. In a preferred aspect of this invention, the number of nucleic acid regions measured for each chromosome is less than 1000. In a most preferred aspect of this invention, the number of nucleic acid regions measured for each chromosome is at least 48 and less than 1000. In one aspect, following the measurement of abundance for each nucleic acid region, a subset of the nucleic acid regions may be used to determine the presence or absence of aneuploidy. There are many standard methods for choosing the subset of nucleic acid regions. These methods include outlier exclusion, where the nucleic acid regions with detected levels below and/or above a certain percentile are discarded from the analysis. In one aspect, the percentile may be the lowest and highest 5% as measured by abundance. In another aspect, the percentile may be the lowest and highest 10% as measured by abundance. In another aspect, the percentile may be the lowest and highest 25% as measured by abundance.

Another method for choosing the subset of nucleic acid regions include the elimination of regions that fall outside of some statistical limit. For instance, regions that fall outside of one or more standard deviations of the mean abundance may be removed from the analysis. Another method for choosing the subset of nucleic acid regions may be to compare the relative abundance of a nucleic acid region to the expected abundance of the same nucleic acid region in a healthy population and discard any nucleic acid regions that fail the expectation test. To further minimize the variation in the assay, the number of times each nucleic acid region is measured may be increased. As discussed, in contrast to the random methods of detecting aneuploidy where the genome is measured on average less than once, the assay systems of the present invention intentionally measures each nucleic acid region multiple times. In general, when counting events, the variation in the counting is determined by Poisson statistics, and the counting variation is typically equal to one divided by the square root of the number of counts. In a preferred aspect of the invention, the nucleic acid regions are each measured on average at least 100 times. In a preferred aspect to the invention, the nucleic acid regions are each measured on average at least 500 times. In a preferred aspect to the invention, the nucleic acid regions are each measured on average at least 1000 times. In a preferred aspect to the invention, the nucleic acid regions are each measured on average at least 2000 times. In a preferred aspect to the invention, the nucleic acid regions are each measured on average at least 5000 times.

In another aspect, subsets of loci can be chosen randomly using sufficient numbers to yield a statistically significant result in determining whether a chromosomal abnormality exists. Multiple analyses of different subsets of loci can be performed within a maternal sample to yield more statistical power. In this example, it may or may not be necessary to remove or eliminate any loci prior to the random analysis. For example, if there are 100 selected regions for chromosome 21 and 100 selected regions for chromosome 18, a series of analyses could be performed that evaluate fewer than 100 regions for each of the chromosomes.

In addition to the methods above for reducing variation in the assay, other analytical techniques, many of which are described earlier in this application, may be used in combination. In general, the variation in the assay may be reduced when all of the nucleic acid regions for each sample are interrogated in a single reaction in a single vessel. Similarly, the variation in the assay may be reduced when a universal amplification system is used. Furthermore, the variation of the assay may be reduced when the number of cycles of amplification is limited.

Use of Percent Fetal Cell-Free DNA to Optimize Aneuploidy Detection

Once the percent fetal cell-free DNA has been calculated, this data may be combined with methods for aneuploidy detection to determine the likelihood that a maternal sample may contain an aneuploidy. In one aspect, an aneuploidy detection methods that utilizes analysis of random DNA segments is used, such as that described in, e.g., Quake, U.S. patent application Ser. No. 11/701,686; Shoemaker et al., U.S. patent application Ser. No. 12/230,628. In a preferred aspect, aneuploidy detection methods that utilize analysis of selected nucleic acid regions are used. In this aspect, the percent fetal cell-free DNA for a sample is calculated. The chromosomal ratio for that sample, a chromosomal ratio for the normal population and a variation for the chromosomal ratio for the normal population is determined, as described herein.

In one preferred aspect, the chromosomal ratio and its variation for the normal population are determined from normal samples that have a similar percentage of fetal DNA. An expected aneuploidy chromosomal ratio for a DNA sample with that percent fetal cell-free DNA is calculated by adding the percent contribution from the aneuploidy chromosome. The chromosomal ratio for the sample may then be compared to the chromosomal ratio for the normal population and to the expected aneuploidy chromosomal ratio to determine statistically, using the variation of the chromosomal ratio, to determine if the sample is more likely normal or aneuploidy, and the statistical probability that it is one or the other.

In a preferred aspect, the selected regions of a maternal sample from an egg donor pregnancy include both regions for determination of fetal DNA content as well as non-polymorphic regions from two or more chromosomes to detect a fetal chromosomal abnormality in a single reaction. The single reaction helps to minimize the risk of contamination or bias that may be introduced during various steps in the assay system which may otherwise skew results when utilizing fetal DNA content to help determine the presence or absence of a chromosomal abnormality.

In other aspects, a selected region or regions may be utilized both for determination of fetal DNA content as well as detection of fetal chromosomal abnormalities. The alleles for selected regions can be used to determine fetal DNA content and these same selected regions can then be used to detect fetal chromosomal abnormalities ignoring the allelic information. Utilizing the same regions for both fetal DNA content and detection of chromosomal abnormalities may further help minimize any bias due to experimental error or contamination.

In certain aspects, percent fetal cell-free DNA may be used as a quality control tool in the determination of the presence of absence of fetal aneuploidy. Determination of percent fetal cell-free DNA in a maternal sample in an egg donor pregnancy can provide a mechanism for determining what, if any, additional analyses can be performed on the sample. In some maternal samples, the level of fetal cell-free DNA in the sample is low, and in some instances may be so low that certain analyses are not able to be reliably performed on the sample, such as analyses to determine the presence of absence of fetal aneuploidy.

In fetal aneuploidy, such as in the case of trisomy 21, a relative increase in Chromosome 21 in the fetal DNA is 50% compared to disomy 21. As a percentage of the total DNA in the maternal sample where, as an example, the fetal DNA is 5% of the total DNA in the sample, the increase in Chromosome 21 as a percentage of the total is 2.5%. As the level of percent fetal cell-free DNA in a sample gets lower, the increase in Chromosome 21 as a percentage of the total DNA in the sample decreases and may be difficult to detect. To assure accurate determination of the presence or absence of fetal aneuploidy, a threshold level of percent fetal cell-free DNA can be used as a quality control tool. A "threshold level" is a minimum level of fetal cell-free DNA that is considered acceptable for performance of additional analysis on the sample, e.g. only maternal samples from egg donor pregnancies with a fetal cell-free DNA level at or above the threshold level are used for determination of the present or absence of fetal aneuploidy. The threshold level may be a predetermined level set prior to the determination of fetal percentage, or may be set following analysis of test performance and/or additional analysis on the desired testing for fetal abnormalities.

Use of a threshold level in analysis of maternal samples from egg donor pregnancies provides a standard to assure quality and reliability of sample analyses. In certain specific examples, a likelihood of the presence or absence of fetal aneuploidy may be determined in samples that can be demonstrated to comprise fetal cell-free DNA at or above a threshold level.

In certain aspects, calculation of percent fetal cell-free DNA in the maternal sample may be performed prior to determination of the presence or absence of fetal aneuploidy. In these aspects, if the percent fetal cell-free DNA does not meet the threshold value, a determination may be made that the sample should not be submitted to additional analyses. Alternatively, further analyses may be performed on the sample, but the results may not be used or may be characterized as unreliable. In certain aspects, calculation of percent fetal cell-free DNA in the maternal sample may be performed simultaneously with determination of the presence or absence of fetal aneuploidy. In these aspects, if the fetal cell-free DNA in the sample is below a threshold value, the determination of the presence or absence of fetal aneuploidy may not be used or may be characterized as unreliable.

In certain aspects, the threshold level of fetal cell-free DNA in a maternal sample may be between 1 and 5% fetal cell-free DNA, such as between 1.5 and 4.5% fetal cell-free DNA, or more specifically between 2 and 4% fetal cell-free DNA. In certain specific aspects, the threshold level of percent fetal cell-free DNA may be 1.0, 1.5, 2.0, 2.5, 3.0, 3.5, 4.0, 4.5 or 5.0% fetal cell-free DNA, or any intervening numbers contained therein.

Detection of Genetic Mutations

In certain aspects, the assay system of the invention detects both fetal aneuploidies and other genetic alterations (including chromosomal abnormalities) in specific loci of interest. Such additional genetic alterations include, but are not limited to, deletion mutations, insertion mutations, copy number polymorphisms, copy number variants, chromosome 22q11 deletion syndrome, 11q deletion syndrome on chromosome 11, 8p deletion syndrome on chromosome 8, and the like. Generally, at least two target nucleic acid sequences present on the same or separate chromosomes are analyzed, and at least one of the target sequences is associated with the fetal allelic abnormality. The sequences of the two target sequences and number of copies of the two target sequences are then compared to determine whether the chromosomal abnormality is present, and if so, the nature of the abnormality.

While much of the description contained herein describes detecting aneuploidy by counting the abundance of nucleic acid regions on one or more putative aneuploid chromosomes and the abundance of nucleic acid regions on one or more normal chromosomes, the same techniques may be used to detect copy number variations where such copy number variation occurs on only a portion of a chromosome. In this detection of the copy number variations, multiple nucleic acid regions within the putative copy number variation location are compared to multiple nucleic acid regions outside of the putative copy number variation location. Other aspects of the invention described for aneuploidy may then be used for the detection of copy number variation. For instance, one may detect a chromosome 22q11 deletion syndrome in a fetus in a mixed maternal sample by selecting two or more nucleic regions within the 22q11 deletion and two or more nucleic acid regions outside of the 22q11 deletion. The nucleic acid regions outside of the 22q11 deletion may be on another region of Chromosome 22 or may be on a completely different chromosome. The abundance of each nucleic acid regions is determined by the methods described in this application.

The nucleic acid regions within the deletion are then quantified to determine a relative frequency as are the nucleic acid regions outside of the deletion. These relative frequencies are then compared to each other to determine the presence or absence of a deletion. Optionally, the relative frequencies are put into a ratio and that ratio may be compared to an average ratio created from a normal population. When the ratio for a sample falls statistically outside of an expected ratio, the deletion is detected. The threshold for the detection of a deletion may be four or more times the variation calculated in the normal population.

Use of Other Fetal Detection Methods

In certain aspects of the invention, the methods of the invention can be used in conjunction with detection of other known risk factors (e.g., maternal age, family history, maternal or paternal genetic information) and/or means for detecting fetal abnormalities, and preferably with other relatively non-invasive diagnostic mechanisms of fetal abnormalities (e.g., measurements of one or more biochemical markers in a maternal sample and/or measurements or structural detection from an ultrasound scan). The combined use of these risk factors and diagnostic mechanisms with the methods of the invention can provide an improved risk determination of fetal abnormality, and in particular the presence or absence of a known genetic mutation such as a trisomy.

Thus, in some preferred aspects the results obtained in the assay systems of the invention are combined with the results from biochemical detection of risk factors, ultrasound detection of risk factors, or other risk determinants of fetal abnormalities.

In some specific aspects, the results obtained in the assay systems of the invention are combined with detection of biochemical markers associated with an increased risk of fetal abnormality. The biochemical markers can be determined based on a sample comprising maternal blood, serum, plasma or urine. Such biochemical markers include but are not limited to free Beta hCG, pregnancy-associated plasma protein A (PAPP-A), maternal blood alpha-fetoprotein, maternal blood hCG, maternal blood unconjugated estriol, maternal blood dimeric inhibin A, maternal urine total estriol, maternal urine beta core fragment, maternal urine hyperglycosylated hCG, maternal blood hyperglycosylated hCG, and inhibin A (preferably dimeric inhibin A). In some aspects, the additional assessment mechanism is multi-marker analysis, such as that described in Orlandi et al., U.S. Pat. No. 7,315,787 or Wald et al. U.S. Pat. No. 6,573,103. Detection of presence and/or levels of these and other markers can be combined with the results from assay systems of the invention to provide a final result to the patient.

In other specific aspects, the results obtained in the assay systems of the invention are combined with the results obtained from ultrasound images, including but are not limited to: nuchal translucency (NT) thickness or edema, nuchal fold thickness, abnormality of the venous system (including the ductus venosus, the portal and hepatic veins and inferior vena cava), absent or hypoplastic nasal bone, femur length, humerus length, hyperechogenic bowel, renal pyelectasis, echogenic foci in the heart, fetal heart rate, and certain cardiac abnormalities. In specific aspects, the additional assessment of fetal abnormality is performed though shape analysis, such as described in U.S. Pat. Nos. 7,780,600 and 7,244,233. In a specific aspect, the additional assessment is based on the determination of landmarks based on images, as described in U.S. Pat. No. 7,343,190. Detection of these and other physical parameters can be combined with the results from assay systems of the invention to provide a final result to the patient.

Most screening markers and physical characteristics are known to vary with gestational age. To take account of this variation each marker level may be expressed as a multiple of the median level (MoM) for unaffected pregnancies of the same gestational age. Especially, for markers derived from ultrasound scans, crown-rump length (CRL) or biparietal diameter (BPD) measurement are alternative measures of gestational age. MoMs may be adjusted in a known way to take account of factors which are known to affect marker levels, such as maternal weight, ethnic group, diabetic status and the number of fetuses carried.

Use of the above techniques can be performed at a single stage of pregnancy or obtained sequentially at two or more different stages of pregnancy. These marker levels can also be interpreted in combination with variables maternal such as maternal age, weight, ethnicity, etc. to derive a risk estimate. The estimation of risk is conducted using standard statistical techniques. For example, known methods are described in Wald N J et al., *BMJ* (1992); 305(6850):391-4; Wald N J et al (1988) *BMJ* 297:883-887 and in Royston P, Thompson S G Stat Med. (1992) 11(2):257-68.

Detection of Other Agents or Risk Factors in Maternal Sample from an Egg Donor Pregnancy Given the multiplexed nature of the assay systems of the invention, in certain aspects it may be beneficial to utilize the assay to detect other nucleic acids that could pose a risk to the health of the subject(s) or otherwise impact on clinical decisions about the treatment or prognostic outcome for a subject. Such nucleic acids could include but are not limited to indicators of disease or risk such as maternal alleles, polymorphisms, or somatic mutations known to present a risk for maternal or fetal health. Such indicators include, but are not limited to, genes associated with Rh status; mutations or polymorphisms associated with diseases such as diabetes, hyperlipidemia, hypercholesterolemia, blood disorders such as sickle cell anemia, hemophilia or thalassemia, cardiac conditions, etc.; exogenous nucleic acids associated with active or latent infections; somatic mutations or copy number variations associated with autoimmune disorders or malignancies (e.g., breast cancer), or any other health issue that may impact on the subject, and in particular on the clinical options that may be available in the treatment and/or prevention of health risks in a subject based on the outcome of the assay results.

Accordingly, as the preferred assay systems of the invention are highly multiplexed and able to interrogate hundreds or even thousands of nucleic acids within a maternal sample, in certain aspects it is desirable to interrogate the sample for nucleic acid markers within the maternal sample, e.g., nucleic acids associated with genetic risk or that identify the presence or absence of infectious organisms. Thus, in certain aspects, the assay systems provide detection of such nucleic acids in conjunction with the detection of nucleic acids for copy number determination within a maternal sample.

For example, in certain maternal samples from egg donor pregnancies, samples from subjects with autoimmune disease, and samples from patients undergoing chemotherapy, the immune suppression of the subject may increase the risk for the disease due to changes in the subject's immune system. Detection of exogenous agents in a maternal sample may be indicative of exposure to and infection by an infectious agent, and this finding have an impact on patient care or management of an infectious disease for which a subject tests positively for such infectious agent.

Specifically, changes in immunity and physiology during pregnancy may make pregnant women more susceptible to or more severely affected by infectious diseases. In fact, pregnancy itself may be a risk factor for acquiring certain infectious diseases, such as toxoplasmosis, Hansen disease, and listeriosis. In addition, for pregnant women or subjects with suppressed immune systems, certain infectious diseases such as influenza and varicella may have a more severe clinical course, increased complication rate, and higher case-fatality rate. Identification of infectious disease agents may therefore allow better treatment for maternal disease during pregnancy, leading to a better overall outcome for both mother and fetus.

In addition, certain infectious agents can be passed to the fetus via vertical transmission, i.e. spread of infections from mother to baby. These infections may occur while the fetus is still in the uterus, during labor and delivery, or after delivery (such as while breastfeeding).

Thus, is some preferred aspects, the assay system may include detection of exogenous sequences, e.g., sequences from infectious organisms that may have an adverse effect on the health and/or viability of the fetus or infant, in order to protect maternal, fetal, and or infant health.

Exemplary infections which can be spread via vertical transmission, and which can be tested for using the assay methods of the invention, include but are not limited to congenital infections, perinatal infections and postnatal infections.

Congenital infections are passed in utero by crossing the placenta to infect the fetus. Many infectious microbes can cause congenital infections, leading to problems in fetal development or even death. TORCH is an acronym for several of the more common congenital infections. These are: toxoplasmosis, other infections (e.g., syphilis, hepatitis B, Coxsackie virus, Epstein-Ban virus, varicella-zoster virus (chicken pox), and human parvovirus B19 (fifth disease)), rubella, cytomegalovirus (CMV), and herpes simplex virus.

Perinatal infections refer to infections that occur as the baby moves through an infected birth canal or through contamination with fecal matter during delivery. These infections can include, but are not limited to, sexually-transmitted diseases (e.g., gonorrhea, chlamydia, herpes simplex virus, human papilloma virus, etc.) CMV, and Group B Streptococci (GBS).

Infections spread from mother to baby following delivery are known as postnatal infections. These infections can be spread during breastfeeding through infectious microbes found in the mother's breast milk. Some examples of postnatal infections are CMV, Human immunodeficiency virus (HIV), Hepatitis C Virus (HCV), and GBS.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

The efficiency and accuracy of identifying percent fetal contribution using the methods of the present invention is demonstrated in the below Examples, where in a group of 24 individuals, the methods correctly determined percent contribution of each individual in the mixed samples.

Example 1: Subjects and Samples

Subjects were prospectively enrolled upon providing informed consent under protocols approved by institutional review boards. Subjects were required to be at least 18 years of age. A subset of enrolled subjects, consisting of 16 individuals consisting of 8 individuals from a first ethnic population and 8 individuals from a second ethnic population, was selected for inclusion in this study. To mimic a mixed sample from an egg donor pregnancy in which the maternal sample comprises DNA from two distinct individuals that do not share approximately half of the genetic information of the other, mixed samples were prepared comprising plasma from one individual from the first ethnic population and one individual from the second ethnic population. For each pairing of individuals, the samples were mixed by volume in fractions of 100%, 95%, 90%, 85%, 15%, 10%, 5%, and 0% of plasma from the individuals from the first ethnic population.

Example 2: Analysis of Polymorphic Loci to Assess Percent Contribution of Unrelated Individuals To assess percent contribution of each individual in the mixed samples, assays were designed against a set of 192 SNP-containing loci on chromosomes 1 through 12, where two middle oligos differing by one base were used to query each SNP. SNPs were optimized for minor allele frequency in the HapMap 3 dataset. Duan, et al., Bioinformation, 3(3):139-41 (2008); Epub 2008 Nov. 9.

Oligonucleotides were synthesized by IDT (Integrated DNA Technologies, Coralville, Iowa) and pooled together to create a single multiplexed assay pool. Assay product was generated from each mixed sample, and products from the mixed samples were pooled and used as template for cluster amplification on a single lane of a TruSeq v2 flow slide (Illumina, San Diego, Calif.). The slide was processed on an Illumina HiSeq 2000 to generate an average of 1.18M raw sequencing reads/sample. An average of 1.15M reads had fewer than 3 mismatches with expected assay structures resulting in an average of 854 reads/locus/sample.

Informative polymorphic loci were defined as loci where at least one allele of a first individual of a mixed sample differed from alleles of a second individual of a mixed sample. Because the assay exhibits allele specificities exceeding 99%, egg donor informative loci were readily identified when the allele proportion of a locus of an individual with lower proportion was measured to be between 1 and 20%. For comparison purposes, two sets of egg donor informative loci were used to analyze the assays for the mixed samples. In the first set of loci, referred to herein as the 'percent contribution non-identical homozygous non-inclusive' set, binomial models were used to remove at least a significant portion of assays from consideration in which alleles from the first individual are homozygous and alleles from the second individual are homozygous but the alleles from the first individual are different from the alleles of the second individual. In the second set of loci, referred to herein as the 'percent contribution non-identical homozygous inclusive' set, no egg donor informative loci were removed from the assay pool. For both sets of loci, a maximum likelihood was estimated using a binomial distribution, such as that described in application 61/509,188, to determine the most likely fetal proportion based upon measurements from several egg donor informative loci. The results correlated well ($R^2 > 0.99$) with the weighted average approach presented by Chu and colleagues (see, Chu, et al., Prenat. Diagn., 30:1226-29 (2010)).

Example 3: Results

Figure 3:
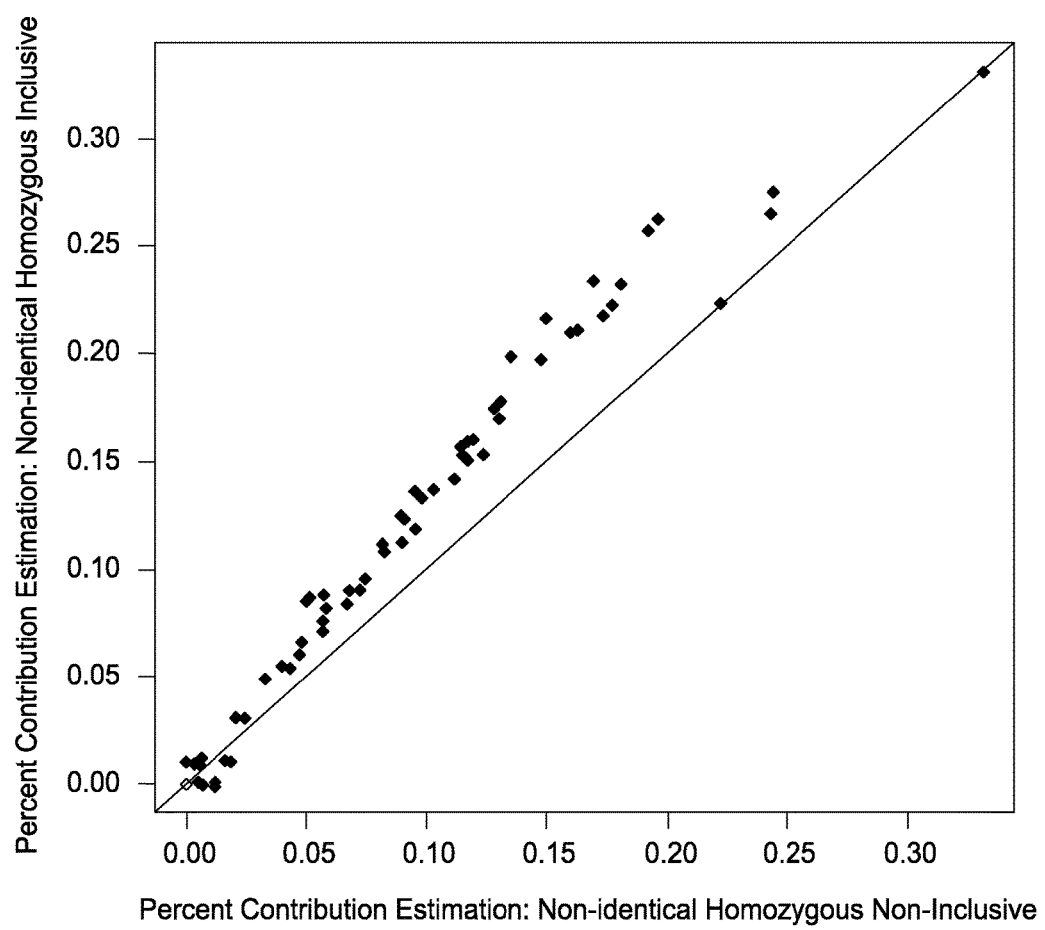
FIG. 3 is a graph of fetal fraction comparisons for the fetal fraction related set and the fetal fraction unrelated set.

FIG. 3 is a graph of percent contribution estimation comparisons for the percent contribution non-identical homozygous inclusive set and the percent contribution non-identical homozygous non-inclusive set. It was expected that the percent contribution non-identical homozygous inclusive set would estimate a higher percent contribution estimation than the percent contribution non-identical homozygous non-inclusive set due to the detected presence of additional polymorphic alleles. With the exception of samples below the detectable limits of the methods (approximately 3.5%), the analysis of the percent contribution non-identical homozygous non-inclusive set showed a lower fetal fraction estimate that the analysis of the percent contribution non-identical homozygous inclusive set.

Example 4: Performance Validation Subjects and Samples

Subjects were prospectively enrolled upon providing informed consent under protocols approved by institutional review boards. Subjects were required to be at least 18 years of age. A subset of enrolled subjects, consisting of 8 individuals consisting of 4 females and 4 males, was selected for inclusion in this study. To mimic a mixed sample from an egg donor pregnancy in which the fetus is a male, mixed samples were prepared comprising plasma from one female and one male. For each female-male pairing, the samples were mixed by volume in fractions of 100%, 95%, 90%, 85%, 15%, 10%, 5%, and 0% of plasma from the female.

Example 5: Performance Validation Analysis of Polymorphic Loci to Assess Percent Contribution of Unrelated Individuals To assess percent contribution of each individual in the mixed samples, assays were designed against a set of 192 SNP-containing loci on chromosomes 1 through 12, where two middle oligos differing by one base were used to query each SNP. SNPs were optimized for minor allele frequency in the HapMap 3 dataset. Duan, et al., Bioinformation, 3(3):139-41 (2008); Epub 2008 Nov. 9.

Oligonucleotides were synthesized by IDT (Integrated DNA Technologies, Coralville, Iowa) and pooled together to create a single multiplexed assay pool. Assay product was generated from each mixed sample, and products from 8 mixed samples were pooled and used as template for cluster amplification on a single lane of a TruSeq v2 flow slide (Illumina, San Diego, Calif.). The slide was processed on an Illumina HiSeq 2000 to generate an average of 1.18M raw sequencing reads/sample. An average of 1.15M reads had fewer than 3 mismatches with expected assay structures resulting in an average of 854 reads/locus/sample.

Informative polymorphic loci were defined as loci where at least one allele of a first individual of a mixed sample differed from alleles of a second individual of a mixed sample. Because the assay exhibits allele specificities exceeding 99%, egg donor informative loci were readily identified when the allele proportion of a locus of an individual with lower proportion was measured to be between 1 and 20%. For comparison purposes, two sets of egg donor informative loci were used to analyze the assays for the mixed samples. In the first set of loci, referred to herein as the fetal fraction related set, binomial functionalities were used to remove assays from consideration in which alleles from the first individual are homozygous and alleles from the second individual are homozygous but the alleles from the first individual are different from the alleles of the second individual. In the second set of loci, referred to herein as the fetal fraction unrelated set, no egg donor informative loci were removed from the assay pool. For both sets of loci, a maximum likelihood was estimated using a binomial distribution, such as that described in application 61/509,188, to determine the most likely fetal proportion based upon measurements from several egg donor informative loci. The results correlated well ($R^2 > 0.99$) with the weighted average approach presented by Chu and colleagues (see, Chu, et al., Prenat. Diagn., 30:1226-29 (2010)).

Example 6: Performance Validation Analysis of Loci on Sex Chromosomes to Assess Percent Contribution of Unrelated Individuals In order to validate the estimation of percent contribution using polymorphic loci, percent contribution was estimated through analysis of loci on the sex chromosomes of each individual in the mixed samples and the results of both estimations were compared. Assays were designed against a set of 8 assays were designed on the sex chromosomes and other assays were designed on chromosomes 13, 18 and 21.

Oligonucleotides were synthesized by IDT (Integrated DNA Technologies, Coralville, Iowa) and pooled together to create a single multiplexed assay pool. Assay product was generated from each mixed sample, and products from the mixed samples were pooled and used as template for cluster amplification on a single lane of a TruSeq v2 flow slide (Illumina, San Diego, Calif.). The slide was processed on an Illumina HiSeq 2000 to generate an average of 1.18M raw sequencing reads/sample. An average of 1.15M reads had fewer than 3 mismatches with expected assay structures resulting in an average of 854 reads/locus/sample.

The unnormalized percent contribution using Y (FPY) was estimated using the median counts of Y assays compared to the median counts of assays on chromosomes 13, 18 and 21.

$$FPY = \frac{\text{median}(Y)}{\text{median}(13, 18, 21)}$$

Since the percent contribution using Y is unnormalized, it was expected that the estimated percent contribution using the polymorphic assays would be strongly correlated, but would not be identical.

Example 7: Performance Validation Results

Figure 4A:
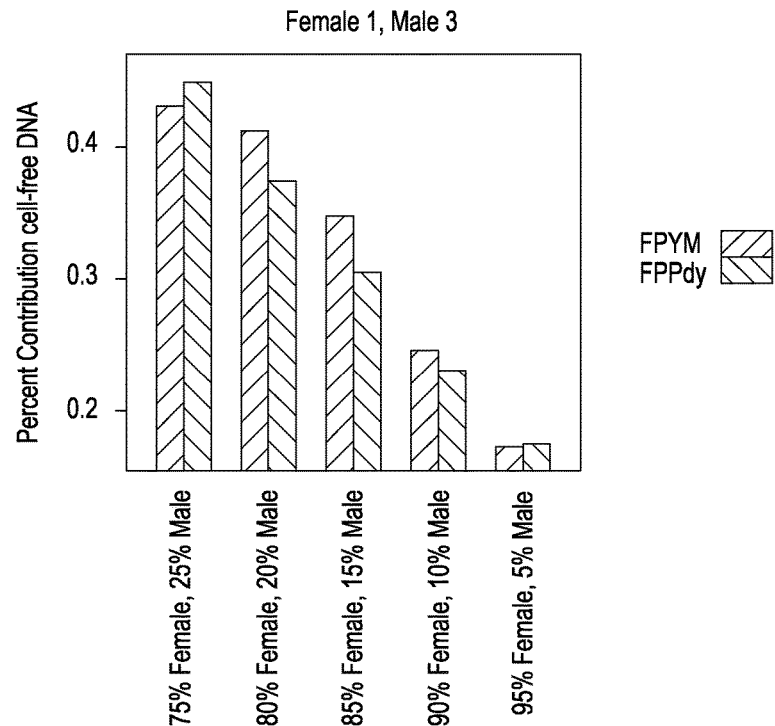
FIGS. 4A-4C are bar graphs comparing the estimated percent contribution using both the polymorphic assays and the sex chromosome assays for the mixed samples comprising 75%, 80%, 85%, 90% and 95% plasma from the female.
Figure 4B:
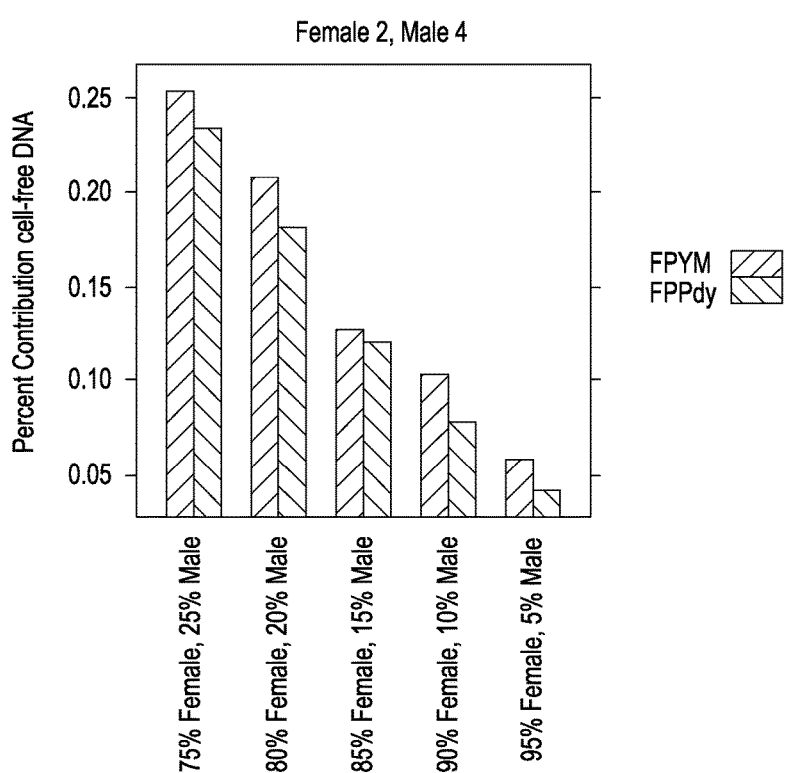
Figure 4C:
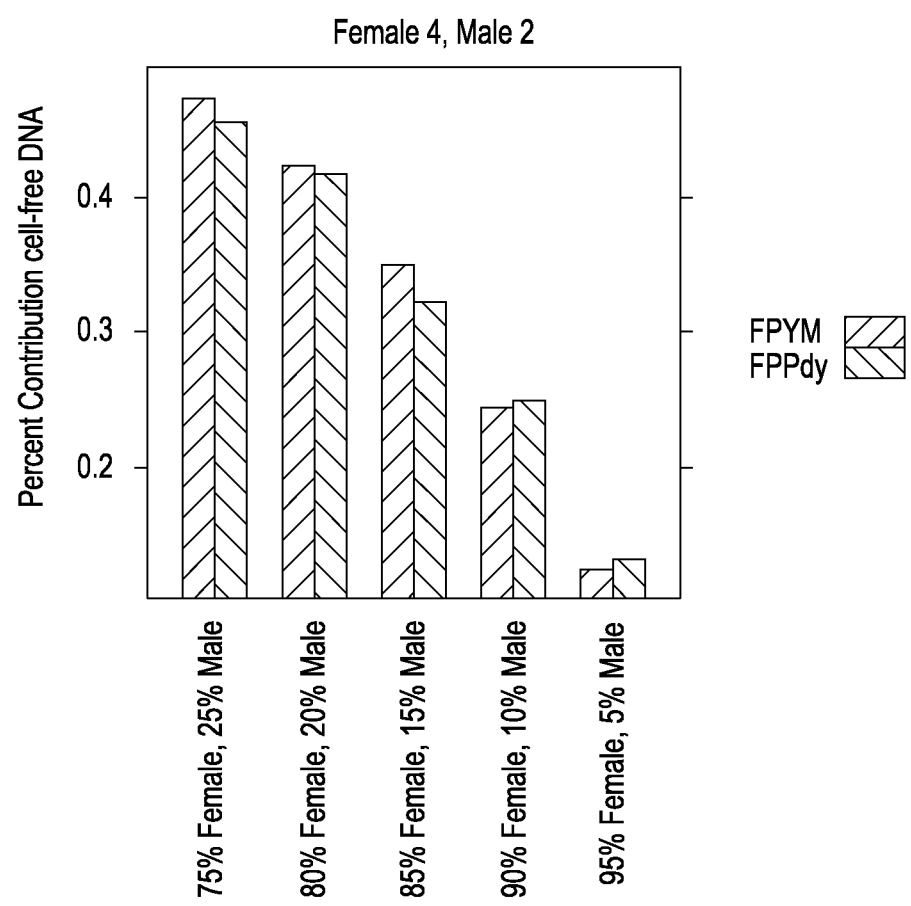

FIGS. 4A-C are bar graphs comparing the estimated percent contribution using both the polymorphic assays and the sex chromosome assays for the mixed samples comprising 75%, 80%, 85%, 90% and 95% plasma from the female. In each of these cases, while the estimation for each mixed sample is not identical, there is a strong correlation between the percent contribution estimation using the polymorphic assays and the estimation using the sex chromosome assays.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, 16.

What is claimed is:

1. A method for detecting the presence or absence of fetal aneuploidy in a pregnant female with an egg donor pregnancy, comprising
    interrogating ten or more nucleic acid regions from a first chromosome from a maternal sample comprising maternal and fetal cell-free DNA, wherein the maternal sample is from the pregnant female;
    detecting the interrogated nucleic acid regions from the first chromosome on average at least 100 times;
    measuring a relative frequency of alleles from the nucleic acid regions from the first chromosome;
    interrogating ten or more selected nucleic acid regions from a second chromosome from the maternal sample;
    detecting the interrogated nucleic acid regions from the second chromosome on average at least 100 times;
    measuring a relative frequency of alleles from the nucleic acid regions from the second chromosome;
    calculating a percent fetal cell-free DNA in the maternal sample by quantifying egg donor informative loci wherein the egg donor informative loci are nucleic acid regions having the following allele patterns: the carrier mother is homozygous and the fetus is heterozygous, the carrier mother is heterozygous and the fetus is homozygous, or the carrier mother is homozygous for one allele and the fetus is homozygous for a different allele;
    measuring the relative frequency of the nucleic acid regions from the first chromosome to the relative frequency of the nucleic acid regions from the second chromosome;
    providing a statistical likelihood of the presence or absence of a fetal aneuploidy using the relative frequency of the nucleic acid regions from the first chromosome and the relative frequency of the nucleic acid region from the second chromosome in view of an expected statistical presence of a first or second aneuploid chromosome using the percent fetal cell-free DNA in the maternal sample.

2. The method of claim 1, wherein calculating percent fetal cell-free DNA comprises selecting egg donor informative loci in which the maternal DNA and the fetal DNA differ in both alleles.

3. The method of claim 1, wherein calculating the percent fetal cell-free DNA comprises comparing a relative frequency of low frequency alleles to a relative frequency of both the high and low frequency alleles.

4. The method of claim 1, wherein calculating the percent fetal cell-free DNA comprises:
- introducing a first set of fixed sequence oligonucleotides to the maternal sample under conditions that allow the fixed oligonucleotides to specifically hybridize to complementary regions in a first polymorphic nucleic acid region;
- introducing a second set of fixed sequence oligonucleotides to the maternal sample under conditions that allow the fixed oligonucleotides to specifically hybridize to complementary regions in a second polymorphic nucleic acid region; and
- ligating the hybridized oligonucleotides to create contiguous ligation products complementary to the nucleic acids.

5. The method of claim 4, wherein the fixed sequence oligonucleotides comprise a universal primer region.

6. The method of claim 4, wherein the first set of fixed sequence oligonucleotides and the second set of fixed sequence oligonucleotides comprises the same universal primer region.

7. The method of claim 4, wherein the first set of fixed sequence oligonucleotides comprises a first universal primer region and the second set of fixed sequence oligonucleotides comprises a second universal primer region.

8. The method of claim 4, and further comprising amplifying the contiguous ligation products using universal primer regions to create amplification products.

9. The method of claim 8, wherein the amplifying comprises performing polymerase chain reaction (PCR) amplification on the contiguous ligation product templates.

10. The method of claim 1, wherein the maternal sample is maternal plasma or serum.

11. The method of claim 1, wherein calculating percent fetal cell-free DNA comprises interrogating twelve or more selected polymorphic nucleic acid regions.

12. The method of claim 11, wherein interrogating twelve or more selected polymorphic nucleic acid regions comprises interrogating at least 20 or more nucleic acid regions.

13. The method of claim 12, wherein interrogating 20 or more selected polymorphic nucleic acid regions comprises interrogating at least 24 nucleic acid regions.

14. The method of claim 13, wherein interrogating 24 or more selected polymorphic nucleic acid regions comprises interrogating at least forty nucleic acid regions.

15. The method of claim 14, wherein interrogating 40 or more selected polymorphic nucleic acid regions comprises interrogating at least ninety nucleic acid regions.

16. The method of claim 15, wherein interrogating 90 or more selected polymorphic nucleic acid regions comprises interrogating at least three hundred nucleic acid regions.

17. The method of claim 1, wherein at least the first chromosome is an autosome.

18. The method of claim 17, wherein both the first and second chromosomes are autosomes.

19. The method of claim 1, wherein detecting the interrogated nucleic acid regions from the first and second chromosome is performed using array-based hybridization processes.

* * * * *